(12) United States Patent
Berg et al.

(10) Patent No.: US 11,764,044 B2
(45) Date of Patent: Sep. 19, 2023

(54) DECONVOLUTION OF MASS SPECTROMETRY DATA

(71) Applicant: Thermo Fisher Scientific (Bremen) GmbH, Bremen (DE)

(72) Inventors: Frank Berg, Bremen (DE); Robert Malek, Lilienthal (DE); Kai Fritzemeier, Stuhr (DE)

( * ) Notice: Subject to any disclaimer, the term of this patent is extended or adjusted under 35 U.S.C. 154(b) by 0 days.

(21) Appl. No.: 17/705,143

(22) Filed: Mar. 25, 2022

(65) Prior Publication Data

US 2022/0277944 A1    Sep. 1, 2022

Related U.S. Application Data

(63) Continuation of application No. 16/884,223, filed on May 27, 2020, now Pat. No. 11,295,940.

(30) Foreign Application Priority Data

May 31, 2019 (GB) .................................. 1907792
Aug. 2, 2019 (EP) .................................... 19189886

(51) Int. Cl.
*H01J 49/00* (2006.01)
*G01N 33/68* (2006.01)

(52) U.S. Cl.
CPC ...... *H01J 49/0036* (2013.01); *G01N 33/6848* (2013.01)

(58) Field of Classification Search
CPC . H01J 49/0036; G01N 33/6848; G01N 27/62; G16H 10/40; G16C 20/30
USPC .................................................. 250/281, 282
See application file for complete search history.

(56) References Cited

U.S. PATENT DOCUMENTS 11,295,940 B2 *   4/2022   Berg .................... H01J 49/0036

* cited by examiner

*Primary Examiner* — Michael Maskell

(57) ABSTRACT

A method for deconvoluting measured mass spectrometry data, the method comprising: receiving measured mass spectrometry data representing at least two molecular moieties each having a respective isotopic pattern, wherein at least two of said isotopic patterns overlap; iteratively filling a set of mass channels to produce an approximated version of the mass spectrometry data, said iterative filling comprising a number of iterations, each iteration comprising filling one or more of the mass channels with a chunk of intensity data according to the isotopic pattern of a respective one of the two or more molecular moieties selected for said iteration; terminating said iterative filling when a fitness criterion is met indicating a fit of the approximated version of the mass spectrometry data to the measured mass spectrometry data; and determining the amount of each molecular moiety that produced the measured mass spectrometry data based on the total amount of fills according to the respective isotopic pattern of said molecular moiety.

14 Claims, 14 Drawing Sheets

DECONVOLUTION OF MASS SPECTROMETRY DATA

PRIORITY

This application is a continuation U.S. patent application Ser. No. 16/884,223, filed May 27, 2020. U.S. patent application Ser. No. 16/884,223 claims the priority benefit of EP Patent Application No. 19189886.5, filed Aug. 2, 2019, the entire disclosure of which is incorporated herein by reference. This application and EP Patent Application No. 19189886.5 claim priority to GB Patent Application No. 1907792.4, filed on May 31, 2019, the entire disclosure of which is incorporated herein by reference.

FIELD

The invention relates to post-acquisition methods for analysing and deconvoluting mass spectrometry data. In particular, the mass spectrometry data comprises overlapping isotopic patterns. The invention is useful for quantitative analysis of mass spectrometry data, in such fields as proteomics, protein analysis, peptide analysis, metabolomics, nucleic acid analysis, compound identification and detection of disease, pharmaceutical and toxicological markers. The invention is particularly, but not exclusively, applicable to analysis of mass spectrometry data that has been acquired using mass tags, such as tandem mass tags (TMTs).

BACKGROUND

Recently there has been development in the area of mass spectrometry in the use of mass tags (also termed mass labels) that are cleavably attached to an associated molecule of interest. The tags are used for the identification and quantification of biological macromolecules, such as proteins, peptides and nucleic acids. The approach of using Tandem Mass Tags (TMTs) is described in WO01/68664 and Thompson et al Anal. Chem. 2003, 75, 1895-1904. TMTs contain four regions or moieties, namely a mass reporter region or moiety (M), a cleavable linker region or moiety (F), a mass normalization region or moiety (N) and a protein reactive group (R). The chemical structures of all the tags are identical but each contains isotopes substituted at various positions, such that the mass reporter and mass normalization regions have different molecular masses in each tag. The combined M-F-N-R regions of the tags have the same total molecular weights and structure so that during chromatographic or electrophoretic separation and in single MS mode, molecules labelled with different tags are indistinguishable. Upon fragmentation in MS/MS mode, sequence information is obtained from fragmentation of the peptide back bone and quantification data are simultaneously obtained from fragmentation of the tags, giving rise to mass reporter ions (https://en.wikipedia.org/w/index.php?title=Tandem_mass_tag&oldid=882091 680).

Real mass tag reagents have impurities as a consequence of the manufacturing process, for example as a result of incomplete labelling or incomplete separation in the manufacturing. Therefore, a mass tag does not only have a single mass, but typically has "satellites" that may interfere (i.e. overlap) with other mass tags used in the same experiment, because the masses may be the same, e.g. the mass of an isotopic variant (isotopologue) of a particular mass tag may be the same as the (main) mass of a different mass tag.

An example of a batch of commercial mass tags may have the following composition (Table1):

| Mass Tag | Reporter Ion | −2 | −1 | Monoisotopic | +1 | +2 |
|---|---|---|---|---|---|---|
| TMT6-126 | 126 | 0 | 0.1 | 100% | 9.4 | 0.6 |
| TMT6-127 | 127 | 0.1 | 0.8 | 100% | 8.6 | 0.4 |
| TMT6-128 | 128 | 0.1 | 1.4 | 100% | 7.2 | 0.5 |
| TMT6-129 | 129 | 0.1 | 1.6 | 100% | 5.7 | 0.3 |
| TMT6-130 | 130 | 0.2 | 2.1 | 100% | 5.1 | 0.2 |
| TMT6-131 | 131 | 0.1 | 4.1 | 100% | 4.7 | 0.1 |

An example of a batch of a commercial tag system with more than one tag ion per nominal mass may have the following composition (Table 2):

| Mass Tag | Reporter Ion | −2 | −1 | Monoisotopic | +1 | +2 |
|---|---|---|---|---|---|---|
| TMT10-126 | 126.127726 | 0.0% | 0.0% | 100% | 5.7% (127C) | 0.0% (128C) |
| TMT10-127N | 127.124761 | 0.0% | 0.2% | 100% | 5.3% (128N) | 0.0% (129N) |
| TMT10-127C | 127.131081 | 0.0% | 0.6% (126) | 100% | 6.4% (128C) | 0.0% (129C) |
| TMT10-128N | 128.128116 | 0.0% | 0.4%(127N) | 100% | 4.1% (129N) | 0.0% (130N) |
| TMT10-128C | 128.134436 | 0.6% (126) | 0.0%(127C) | 100% | 3.0% (129C) | 0.0% (130C) |
| TMT10-129N | 129.131471 | 0.1% (127N) | 0.8%(128N) | 100% | 3.1% (130N) | 0.0% (131) |
| TMT10-129C | 129.137790 | 0.0% (127C) | 1.4%(128C) | 100% | 2.4% (130C) | 0.0% |
| TMT10-130N | 130.134825 | 0.1% (128N) | 1.5%(129N) | 100% | 2.4% (131) | 3.2% |
| TMT10-130C | 130.141145 | 0.0% (128C) | 1.8%(129C) | 100% | 2.1% | 0.0% |
| TMT10-131 | 131.138180 | 0.0% (129N) | 1.8%(130N) | 100% | 1.7% | 0.0% |

Most labels have only a small component outside the main peak, but up to four satellites are present, in this case for the 130N reporter ion. Depending on the preparation method, there may be relationships only between certain subsets (i.e. the "N" labels have "N-type" satellites and the "C" labels have "C-type" satellites).

It is generally known how such overlaps of mass spectral features can be resolved, e.g. as described in Biemann, MASS SPECTROMETRY Organic Chemical Applications, McGRAW-HILL 1962; Goraczko, Journal of Computational Chemistry, Vol. 22, No. 3, 354-365 (2001); U.S. Pat. No. 7,193,705 (Schluter); and U.S. Pat. No. 7,105,806 (Pappin). For example, U.S. Pat. No. 7,105,806 discloses isotope deconvolution for overlapping tandem mass tags and algorithms that subtract the influence of satellites of neighbouring mass tags. The common algorithms described in the references above are all basic ways of building a system of linear equations from the known isotopic distributions $S_j^i$ of the individual mass tags and the measured spectrum $M_p$ and solving it for the amounts (or concentrations) $C_q$ of the mass tags, i.e.

$$\begin{pmatrix} S_0^1 & S_{-1}^2 & S_{-2}^3 & \cdots & \\ S_1^1 & S_0^2 & S_{-1}^3 & \cdots & \\ S_2^1 & S_1^2 & S_0^3 & \cdots & \\ \vdots & S_2^2 & S_{+1}^3 & \cdots & \\ \vdots & \vdots & S_{+2}^3 & \cdots & S_{-l}^n \\ \vdots & \vdots & \vdots & \ddots & \vdots \\ & \cdots & \cdots & \cdots & S_{+k}^n \end{pmatrix} \begin{pmatrix} C_1 \\ C_2 \\ C_3 \\ \vdots \\ C_n \end{pmatrix} = \begin{pmatrix} M_1 \\ M_2 \\ M_3 \\ \vdots \\ M_m \end{pmatrix} \quad \text{(eq. 1)}$$

This system is then solved with known linear algebra methods such as the Gaussian algorithm, SV or LU decomposition or various approximations, including a slightly modified Thomas-Algorithm in U.S. Pat. No. 7,105,806. A fast approximation may be found by ignoring all contributions except the first satellite peaks on either side and using the Thomas Algorithm (https://en.wikipedia.org/w/index.php?title=Tridiagonal_matrix_algorithm&oldid=880475866). In practice, various factors complicate solving of the problem. For example, the measured spectra may have additional intensity contributions from instrument or chemical noise, which have an adverse effect on the accuracy of the numeric solution (especially in case of a "naïve" Gaussian or Thomas approach); the analysis may have to be applied to thousands of spectra in LC/MS experiments; and the amount of satellite peaks may be fairly high for mass tag kits with a high number of different tags (e.g. 10 or more tags).

SUMMARY

According to an aspect of the invention there is provided a method for deconvoluting measured mass spectrometry data comprising overlapping isotopic patterns of at least two molecular moieties.

According to a first aspect of the invention there is provided a method for deconvoluting measured mass spectrometry data, the method comprising: receiving measured mass spectrometry data representing at least two molecular moieties each having a respective isotopic pattern, wherein at least two of said isotopic patterns overlap; iteratively filling a set of mass channels to produce an approximated version of the mass spectrometry data, said iterative filling comprising a number of iterations, each iteration comprising filling one or more of the mass channels with a chunk of intensity data according to the isotopic pattern of a respective one of the two or more molecular moieties selected for said iteration; terminating said iterative filling when a fitness criterion is met indicating a fit of the approximated version of the mass spectrometry data to the measured mass spectrometry data; and determining the amount of each molecular moiety that produced the measured mass spectrometry data based on the total amount of fills according to the respective isotopic pattern of said molecular moiety.

In some embodiments for each iteration (a) the chunk of intensity data comprises a set of intensities each corresponding to a respective mass channel, wherein the set of intensities is scaled according the isotopic pattern for the intensity data; or (b) the chunk of intensity data is an intensity for a respective mass channel, wherein the respective mass channel is selected according to a probability distribution based on the isotopic pattern for the intensity data.

The molecular moiety selected for each iteration may be selected based on a measure of discrepancy between the measured mass spectrometry data and the approximated version of the mass spectrometry data at said iteration.

The mass spectrometry data is typically a mass spectrum. In another aspect the method may comprise receiving the measured mass spectrometry data, i.e. generated from a mass spectrometry experiment. The mass spectrometry data may be received directly from the experiment or may be received from a library of stored mass spectrometry data generated from earlier mass spectrometry experiments. The method may comprise identifying a plurality of mass channels 1 . . . n within the mass spectrometry data. The mass channels may correspond to, i.e. represent, the masses of the molecular moieties (i.e. nominal or monoisotopic masses) and/or the mass channels may correspond to peaks in the measured mass spectrometry data. The method may comprise forming simulated mass spectrometry data (producing a simulated mass spectrum), i.e. performing a simulation of the measured mass spectrometry data, by iteratively filling the mass channels with chunks of mass spectrometry data (specifically, chunks of isotopic data), wherein each chunk comprises the isotopic pattern of one of the molecular moieties. A chunk of isotopic data thus typically comprises intensities for the monoisotopic mass and each isotopic satellite mass (isotopic mass) for one of the molecular moieties. The size or magnitude (i.e. the intensity) of each chunk refers to the size (i.e. intensity) of the chunk in the mass channel that represents the molecular moiety. The chunk size is preferably greater than the noise determined in the measured mass spectrometry data. The size or magnitude (i.e. the total intensity) of each chunk is selected depending on the desired accuracy of the method, smaller (lower intensity) chunks generally providing more accurate deconvolution but making the process longer. The chunk size may be fixed or variable as described below.

In preferred embodiments, at each iteration, the chunk of isotopic data used for filling comprises the isotopic pattern of the molecular moiety having a mass corresponding to the mass channel with the largest difference (in intensity) between the simulated mass spectrometry data and the measured mass spectrometry data. However, in other embodiments, the simulated spectrum may be filled with the chunks of isotopic data of the molecular moieties according to another criteria, e.g. in order of their ascending (or descending) mass channel. A fill with a chunk of mass spectrometry isotopic data may be rejected if it results in the intensity in a mass channel of the simulated mass spectrometry data being greater, above a defined tolerance, than the intensity in the mass channel of the measured mass spectrometry data. The tolerance is preferably no greater than the chunk size in the mass channel and is typically less than the chunk size. The tolerance can be zero in some cases. The chunk size here refers to the minimum chunk size used when the chunk size is variable. The iteration then continues with the next mass channel, for example according to the difference criteria. The iterative process may be terminated (i.e. the simulation is terminated) when a fitness criterion is met. The fitness criterion may be met when filling is rejected for all mass channels, i.e. when a chunk comprising the isotopic pattern of any of the molecular moieties is rejected. Another fitness criterion may be met when the total intensity distributed by the chunks of isotopic data is equal to the sum of the intensities (i.e. for all mass channels) in the measured mass spectrometry data or spectrum. Another fitness criterion may be met when no mass channel has a difference between the simulation and the measured mass spectrometry data or spectrum that is larger than or equal to the minimum chunk size used. Another fitness criterion may be met when the intensities in all mass channels of the simulation are within a defined tolerance compared to the measured mass spectrometry data or spectrum.

The amount of fills with each isotopic pattern (for each molecular moiety or mass channel that represents that moiety) can be tracked or recorded and the sum for each can be determined to be the amount or concentration of the molecular moiety. In other words, the method comprises determining the amount of each molecular moiety that produced the measured mass spectrometry data based on the total amount of fills in the simulation with the isotopic pattern of each molecular moiety. The amount of fills with the isotopic pattern of each molecular moiety may be simply the number of fills for that moiety when the chunk size or magnitude is fixed for all chunks. However, when a variable chunk size is used (or a fixed chunk size), as described below, the amount of fills may be the total intensity provided by all the fills for each molecular moiety (i.e. the sum of the chunk sizes for all the fills for each molecular moiety). The results of the method, such as the amounts or concentrations of the molecular moieties, can be output and/or stored in a database.

The identity and thus the isotopic pattern of the molecular moieties is generally known. The isotopic pattern means the relative intensities of each isotopic peak of the molecular moiety.

The molecular moieties may be mass tags or derived from mass tags (e.g. fragments of mass tags), preferably tandem mass tags (TMTs). In particular, the molecular moieties may be fragments of mass tags, such as mass reporter moieties of TMTs. In such embodiments, the isotopic pattern for each tag is typically mainly derived from the manufacturing process of the mass tag and is generally known, for example as indicated above in Tables 1 and 2.

In other cases, the molecular moieties may be other entities (e.g. not mass tags) with known or approximately known relative isotopic intensities, e.g. for deconvolution of overlapping isotopic patterns of multiply charged peptides relative intensities based on an average isotopic composition of peptides may be used (M. W. Senko, S. C. Beu, and F. W. McLafferty, "Determination of Monoisotopic Masses and Ion Populations for Large Biomolecules from Resolved Isotopic Distributions," *J. Am. Soc. Mass Spectrom.*, vol. 6, pp. 229-233, June 2017.)

The invention provides methods for the deconvolution of mass spectrometry data, particularly mass spectrometry data which comprises overlapping isotopic patterns. In certain aspects, the invention provides methods for the deconvolution of mass tags in mass spectrometry data, especially tandem mass tags (TMTs).

The invention is thus useful in the analysis of data obtained using mass spectrometry to detect mass tags (also termed mass labels) that are cleavably attached to an associated molecule of interest. Such methods of mass spectrometry using Tandem Mass Tags (TMTs) are described in WO01/68664 and Thompson et al Anal. Chem. 2003, 75, 1895-1904. The invention provides post-acquisition methods for analysing the mass spectrometry data.

The invention may be used for deconvolution of overlapping isotopic patterns in mass spectrometry data generally, in particular when the contributing isotopic patterns (sub-patterns) are known.

Mass spectrometric data may be obtained, for example, by one of MS, GC/MS, LC/MS, IMS/MS, DIMS/MS, wherein the "MS" collectively denotes mass spectrometry, including MS/MS or MSn methods, "GC" denotes gas chromatography, "LC" denotes liquid chromatography, "IMS" denotes ion mobility spectrometry and "DIMS" denotes differential ion mobility spectrometry. Combinations are possible, e.g. LC/IMS/MS etc.

The data is generally obtained as an output from a mass spectrometer. Embodiments of the invention thus may comprise performing mass analysis of one or more samples, in particular biological samples, using a mass spectrometer to obtain the measured mass spectrometry data. The biological samples may contain one or more molecules of interest, such as one or more proteins, peptides, or nucleic acids. The molecules of interest may be mass tagged, for example using TMTs. Preferably molecules of interest are tagged using isobaric mass tags, such as TMTs. The one or more samples may comprise mass tags or moieties of mass tags that have been cleaved from the molecules of interest. In some embodiments, the mass spectrometry data may be generated by fragmentation of mass tags, such as TMTs. The mass tags may have been cleaved from one or more molecules of interest. The fragmentation of the mass tags can occur by subjecting the mass tag and/or the mass tagged molecules of interest to dissociative energy (e.g., in collision-induced dissociation (CID)). Preferably the mass tags that have been cleaved from the molecules of interest are analysed, but alternatively the quantitative analysis may be performed on the peptides with the other parts of the mass labelling agents.

Another aspect of the invention provides a computer program which, when executed by one or more processors, causes the one or more processors to carry out a method according to the invention. The computer program may be stored on a computer-readable medium.

The invention may be carried out using a computer, i.e. computer implemented. In embodiments, the computer can comprises: a storage medium, a memory, a processor, one or more interfaces, such as a user output interface, a user input interface and a network interface, which are linked together, e.g. over one or more communication buses.

The storage medium may be any form of non-volatile data storage device such as one or more of a hard disk drive, a magnetic disc, an optical disc, a ROM, etc. The storage medium may store one or more computer programs, including a program according to the invention.

The memory may be any random access memory (storage unit or volatile storage medium) suitable for storing data and/or computer programs.

The processor may be any data processing unit suitable for executing one or more computer programs (such as those stored on the storage medium and/or in the memory), some of which may include one or more computer programs according to embodiments of the invention or computer programs that, when executed by the processor, cause the processor to carry out a method according to an embodiment of the invention. The processor may comprise a single data processing unit or multiple data processing units operating in parallel, separately or in cooperation with each other. The processor, in carrying out data processing operations for embodiments of the invention, may store data to and/or read data from the storage medium and/or the memory.

An interface may be provided that is any unit for providing an interface between the computer and a device external to, or removable from, the computer. The external device may be a data storage device, for example, one or more of an optical disc, a magnetic disc, a solid-state-storage device, etc. The interface may therefore access data from, or provide data to, or interface with, the external device in accordance with one or more commands that it receives from the processor.

A user input interface may be arranged to receive input from a user, or operator. The user may provide this input via one or more input devices of the system, such as a mouse (or other pointing device) and/or a keyboard, that are connected to, or in communication with, the user input interface. However, it will be appreciated that the user may provide input to the computer via one or more additional or alternative input devices (such as a touch screen). The computer may store the input received from the input devices via the user input interface in the memory for the processor to subsequently access and process, or may pass it straight to the processor, so that the processor can respond to the user input accordingly.

Information about the isotope patterns may be input by the user via the means above, or may be made available to the computing device in machine readable form, e.g. by a QR or bar code, which may be scanned or read, by download through a network, by RFID tags attached to vials containing the TMT or other labelling agents, or by combinations thereof (e.g. downloading information about the labels and their respective masses and impurities/satellite peaks in response to a QR code on a product packaging which is scanned manually by a user or automatically by a lab automation appliance), or any other means available for transfer of information.

A user output interface may be arranged to provide a graphical/visual output to a user, or operator. As such, the processor may be arranged to instruct the user output interface to form an image/video signal representing a desired graphical output, and to provide this signal to a video display unit (VDU) such as a monitor (or screen or display unit) that is connected to the user output interface.

A network interface may be arranged to provide functionality for the computer to download data from and/or upload data to one or more data communication networks.

Output information may be generated or provided anywhere within a local or distributed computing system, including e.g. cloud storage, provision for display of direct or derivative results on mobile devices, or transfer in machine readable form or as a data stream to other post-processing tools.

It will be appreciated that the architecture of the computer system described above is merely exemplary and that other computer systems with different architectures (for example with fewer components or with additional and/or alternative components may be used). As examples, the computer could comprise one or more of: a personal computer; a server computer; a laptop; etc.

In view of the above, certain preferred embodiments of the invention include:
 a method for deconvoluting measured mass spectrometry data comprising overlapping isotopic patterns of at least two molecular moieties, comprising:
  identifying a plurality of mass channels within the mass spectrometry data that correspond to the masses of the molecular moieties; producing a simulation of the measured mass spectrometry data by iteratively filling the mass channels with chunks of isotopic data, wherein each chunk comprises the isotopic pattern of one of the molecular moieties;
  terminating the simulation when a fitness criterion is met for the mass channels indicating a fit of the simulation to the measured mass spectrometry data; and determining the amount of each molecular moiety that produced the measured mass spectrometry data based on the total amount of fills in the simulation with the isotopic pattern of each molecular moiety.

Preferably at each iteration, the chunk of isotopic data used for filling comprises the isotopic pattern of the molecular moiety having a mass corresponding to the mass channel with the largest difference in intensity between the simulated mass spectrometry data and the measured mass spectrometry data.

Preferably the method further comprises rejecting a fill from the simulation if it results in the intensity in a mass channel of the simulated mass spectrometry data being greater than the intensity in the mass channel of the measured mass spectrometry data above a defined tolerance.

Preferably the fitness criterion is met by any of the following:
 (i) when filling is rejected for all mass channels;
 (ii) when a total intensity contributed by the chunks of isotopic data is equal to the sum of the intensities for all mass channels in the measured mass spectrometry data or spectrum;
 (iii) when no mass channel has a difference between the simulation and the measured mass spectrometry data that is equal to or larger than a minimum chunk size;
 (iv) when intensities in all mass channels of the simulation are within a predefined maximum tolerance compared to the measured mass spectrometry data Preferably the size of each chunk is selected depending on the desired accuracy of the method.

Preferably the size of each chunk is 0.1% to 1% of the most intense measured peak $M_p$ in the measured mass spectrometry data.

Preferably the simulation comprises starting the fills with chunks of isotopic data of a larger size and reducing the chunk size as the simulation approaches the measured mass spectrometry data.

Preferably a noise level in the measured mass spectrometry data is used for determination of the defined tolerance used in the fitness criterion of the simulation.

Preferably prior to iteratively filling the mass channels with chunks of isotopic data, the simulation is pre-filled with a known background intensity of the measured mass spectrometry data.

Preferably the molecular moieties are mass tags or fragments derived from mass tags. Preferably the molecular moieties are tandem mass tags or fragments derived from tandem mass tags. Preferably the molecular moieties are mass reporter moieties of tandem mass tags.

Certain preferred embodiments of the invention may provide a computer program, stored on a computer-readable medium, which, when executed by one or more processors, causes the one or more processors to carry out the method according to any preceding claim.

According to another aspect of the invention, there is provided an apparatus arranged to carry out a method according to any embodiment of the invention as described above.

DETAILED DESCRIPTION

The measured mass spectrometry data typically comprises a mass spectrum, which term includes a partial mass spectrum covering a limited mass range, and the method will be described with reference to a measured mass spectrum. In certain aspects, the method is based on using an iteration (or iterative) process for forming an approximated (or simulated) mass spectrum that approximates to the measured mass spectrum $M_p$ that inherently fulfils the following conditions:

All solutions $C_q$ (amounts or concentrations of the molecular moieties) are positive (or zero), i.e. negative solutions are not produced.

Approximated simulated spectra are formed by adding assumed components $S_j^i \cdot C_i$ ($S_j^i$ are the known isotopic distributions across the mass channels j of the individual molecular moieties i—i.e. $S_j^i$ gives the relative expected intensity at the mass channel for $M_j$ for a moiety having the quantification channel for $C_i$)

The method is stable against noise or background, i.e. contributions to the measured mass spectrum $M_p$ that are not due to the molecular moieties.

Figure 1A:
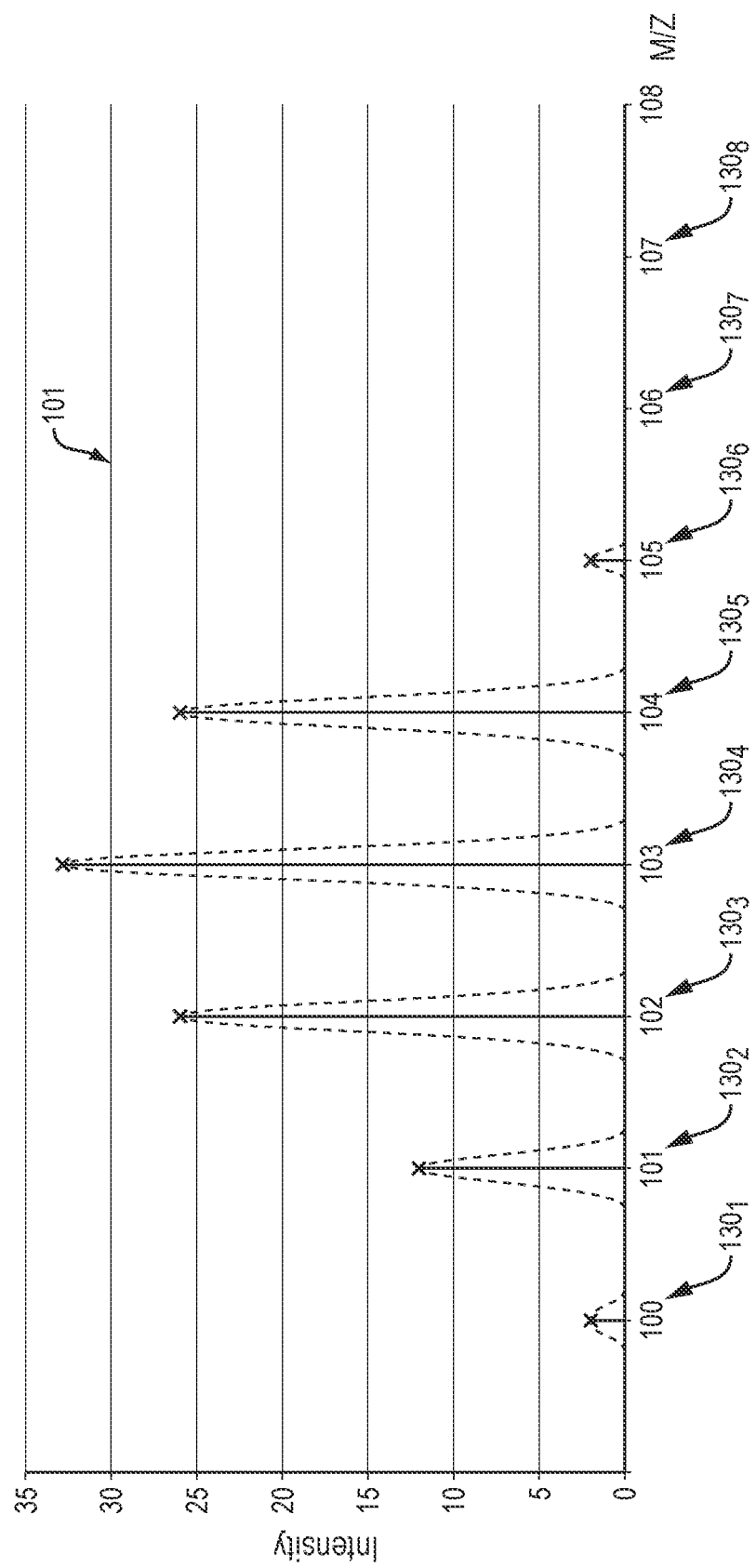
FIG. 1a shows an example graphical representation of mass spectrometry data in the form of a mass spectrum.

FIG. 1a shows an example graphical representation of mass spectrometry data 101 in the form of a mass spectrum.

The mass spectrometry data 101 can be represented in the form of one or more mass channels $130_i$ (where i is simply an index which runs from 1 to n). Each mass channel corresponds to a respective mass value (or mass to charge ratio, referred to herein as m/z value) at which ionic species of the same mass (or mass to charge ratio) are detected in a mass spectrometry experiment. The intensity (or relative abundance), $M_i$, measured by the mass spectrometry equipment for a given mass channel $130_i$ correlates to the relative abundance of ionic species having the mass (or m/z value) detected by the mass spectrometry equipment.

It will be appreciated that there may be more than one ionic species detected in a given mass spectrometry experiment with the same mass (or m/z value). As such the intensity value for a given mass channel may represent the sum of the abundances of all of the ionic species detected in a given mass spectrometry experiment with the mass (or m/z value) corresponding to that particular mass channel.

An experimental mass spectrum such as in the mass spectrometry data 101 may be plotted in the form of a continuum plot, indicated by the dashed line, and a centroid plot, indicated by the vertical solid lines. The widths of peaks indicated by the dashed line represent the limit of the mass resolving power, which is the ability to distinguish two different ionic species with close m/z ratios. In this way it will be understood that a mass channel may include the intensities of all detected ionic species having m/z values that are the same as that of the mass channel to within a given resolution of mass spectrometry equipment (or experiment itself). In other words when we refer herein to m/z values being the same (or equal) the skilled person will appreciate that this may be the same to within a given resolution of the relevant mass spectrometry experiment.

However it will be appreciated that the mass spectrometry data 101 does not need to be plotted in the form of a graph. Indeed, the mass spectrum may be represented in any suitable form. For example, the mass spectrum may be represented as a list comprising the one or more intensity values and the one or more m/z values. In some cases the mass spectrum may simply be represented as a list of centroids (or local maxima), each centroid being represented as an m/z value and intensity value pair.

As there are many techniques commonly used in the art for obtaining such centroids from mass spectrometry data these will not be discussed further herein. However, it will be appreciated that the techniques described herein may be performed on lists of centroids forming mass spectrometry data 101, or on raw mass spectrometry data 101 where suitable techniques are used to identify the intensity maxima (or centroids). In some cases such centroids or "stick spectruma" may be the result of aggregation of information across multiple spectra from a chromatographic peak.

Figure 1B:
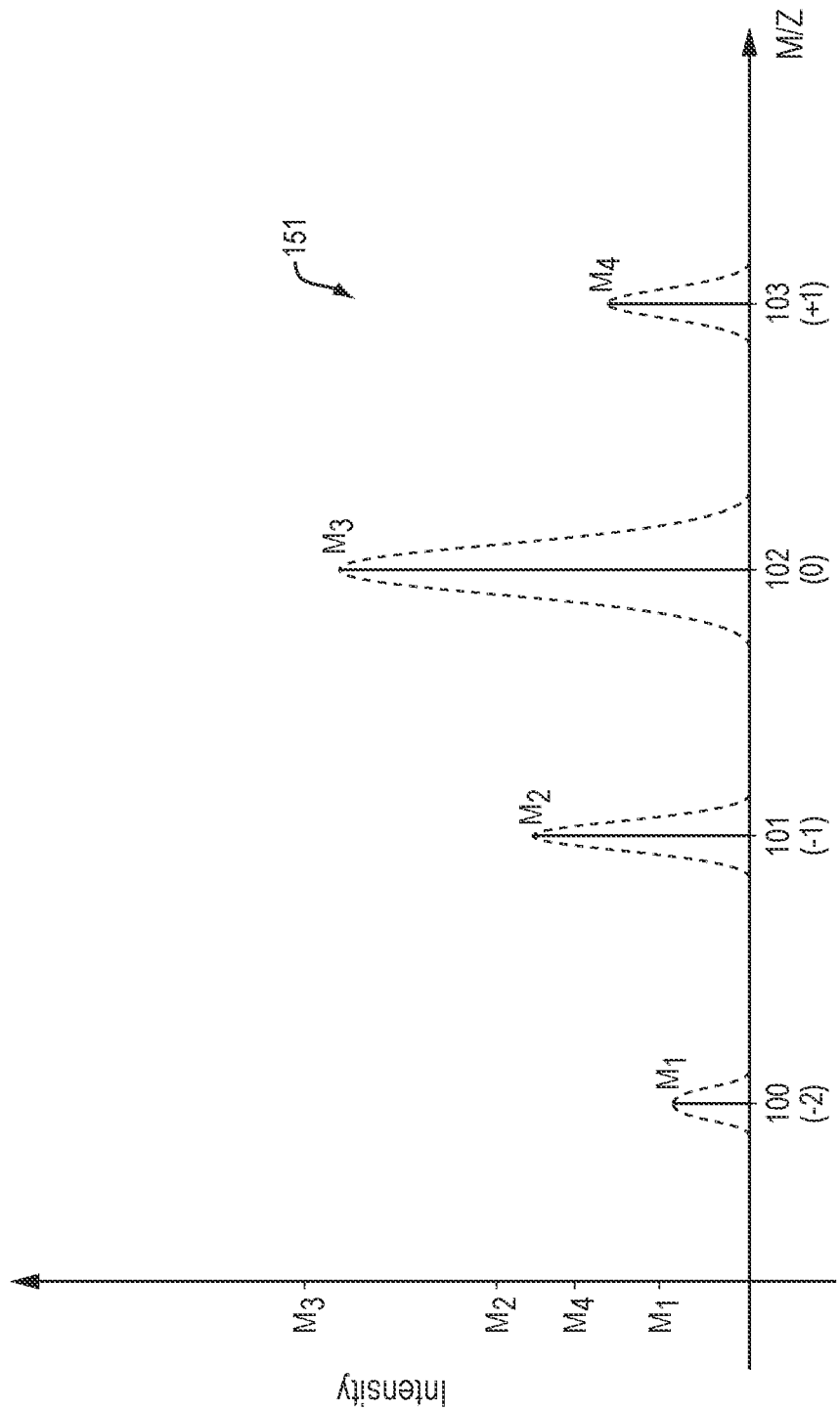
FIG. 1b shows an example graphical representation of mass spectrometry data for a single molecular moiety.

FIG. 1b shows an example graphical representation of mass spectrometry data 151 for a single molecular moiety as described previously. Again the graphical representation of the mass spectrometry data 151 is in the form of a mass spectrum.

As described previously a particular molecular moiety may in a mass spectrometry experiment have a main isotope with a main mass (or m/z value) and one or more other isotopes (often known as satellites or satellite isotopes) having different respective masses (or m/z values). This can lead to the mass spectrum for a particular molecular moiety having a number of m/z intensity peaks, as shown in the mass spectrum 151 in FIG. 1b. Typically, in mass tagging, the mass with the highest intensity for a given moiety is regarded as the main mass (or reporter mass, or tag mass) for that moiety or tag. The masses of the remaining intensity peaks are then usually regarded as the satellite masses. A common notation in the art is to label the main mass as "0" the adjacent satellite with a higher mass as "+1", the next higher mass satellite "+2" and so on. Similar in terms of decreasing mass (relative to the main mass) the adjacent satellite is typically labelled "−1" the next lower mass satellite "−2" and so on.

In this particular example, the mass spectrometry data 151 of FIG. 1b shows four mass channels with non-zero intensities. The main mass channel is at 102 and has the intensity $M_3$. The "−1" satellite gives rise to an intensity $M_2$ at the mass channel 101. The "−2" satellite gives rise to an intensity $M_1$ at the mass channel 100. Finally, the "+1" satellite gives rise to an intensity $M_4$ at the mass channel 103.

The overall concentration (or abundance, or intensity) of the moiety is proportional to the sum of the intensities of the main mass channel and the satellite mass channels. In this particular example the concentration of the moiety is given by $\Sigma_{i=1}^{4} M_i$. The mass channel for (or assigned to, or used to label) a given moiety is typically referred to as the "quantification channel", (having an intensity or concentration $C_j$), and usually corresponds to the main mass channel (having an intensity $M_j$), of the moiety. This quantification channel is filled with the overall concentration for the moiety. A "corrected" mass spectrum of a molecular moiety may be plotted which consists of the overall concentration of the moiety plotted as a single peak at the quantification channel.

It will also be appreciated that the intensities of the isotopes for a given moiety represent (or provide or comprise) an isotopic pattern. An isotopic pattern will be understood as the pattern of relative abundancies of a number of isotopes of a particular molecular moiety. As such, an isotopic pattern may allow calculation of the relative abundancy of one isotope of a particular molecular moiety with respect to another isotope of the particular molecular moiety. An isotopic pattern for a molecular moiety may, therefore, comprise (or represent) a number of mass channels, each mass channel corresponding to a respective isotope of the molecular moiety. The isotopic pattern further comprises a respective intensity (or abundance) for each mass channel of the isotopic pattern.

An isotopic pattern may be represented by (or may comprise) a set of coefficients, $S_p$, relating the expected intensity at a given mass channel, $M_p$, for an overall concentration, C, of a given molecular moiety. In other words the coefficients may obey the relation $M_p \propto S_p C$. In the case where the coefficients are normalized so that they sum to unity the stronger relation $M_p = S_p C$ would be obeyed. Another common normalization for an isotopic pattern is to scale the coefficients such that $S_j = 1$, where $M_j$ is the main or reporter mass channel (i.e. the concentration channel is $C_j$). It will be appreciated that there are numerous mathematically equivalent ways in which such coefficients may be constructed depending upon the units used for the various quantities, and/or the normalization scheme used.

In this way it would be appreciated that, an overall concentration of a molecular moiety may be scaled by the isotopic pattern to obtain expected mass spectrometry data comprising expected intensities for the mass channels of the isotopes of said moiety.

Figure 1C:
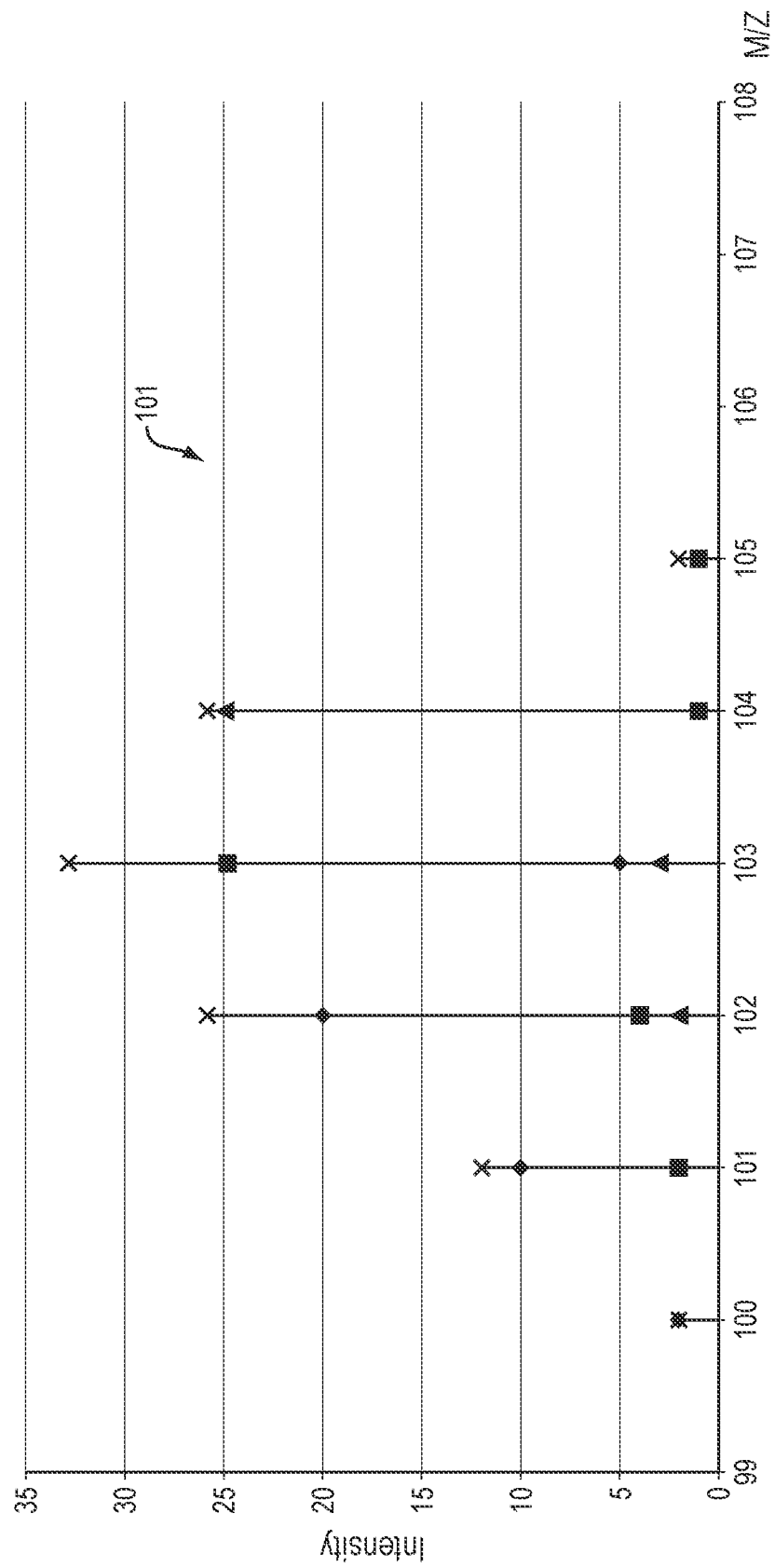
FIG. 1c shows the mass spectrometry data of FIG. 1a in terms of overlapping mass spectrometry data for individual moieties.

FIG. 1c shows the mass spectrometry data 101 of FIG. 1a in terms of overlapping mass spectrometry data for individual moieties. The discussion of the mass spectrometry data 101 set out above in relation to FIG. 1a applies equally here. The dotted line showing the continuum plot from FIG. 1a has been omitted to improve readability.

In addition, FIG. 1c shows that the mass spectrometry data 101 is produced by (or represents or has present) a number of molecular moieties. FIG. 1c shows the presence of a first moiety (represented by the diamond symbols) with a main mass channel at the mass 102, corresponding to the mass channel of intensity $M_3$ of the mass spectrometry data 101. A second moiety (represented by the square symbols) is shown having a main mass channel at the mass 103, corresponding to the mass channel of intensity $M_4$ of the mass spectrometry data 101. Finally, a third moiety (represented by the triangle symbols) is shown having a main mass channel at the mass 104, corresponding to the mass channel of intensity $M_4$ of the mass spectrometry data 101. As in FIG. 1a the actual measured centroids are shown by the cross symbols and these, in this case, are simply the sum of the intensities of the moieties at each mass channel. In real world data it will be appreciated that contributions from noise and equipment error will typically also be present in the mass channel in the measured centroids.

As can be seen from FIG. 1c the isotopic patterns of the three molecular moieties overlap. In other words, at least one isotope of one moiety has the same mass as an isotope of another moiety. It will be appreciated that in this case the same mass is defined with reference to the resolution of the mass spectrometry data—i.e. the two isotopes cannot be resolved separately. In this way at the intensities of at least some of the mass channels of the mass spectrometry data include contributions from different moieties. In particular:

the intensity $M_2$ of the mass channel having the mass 101 is the sum of the intensity of the "−2" satellite of the second moiety and the intensity of the "−1" satellite of the first moiety;

the intensity $M_3$ of the mass channel having the mass 102 is the sum of the intensity of the "−2" satellite of the third moiety, the intensity of the "−1" satellite of the second moiety, and the intensity of the main isotope of the first moiety;

the intensity $M_4$ of the mass channel having the mass 103 is the sum of the intensity of the "+1" satellite of the first moiety, the intensity of the "−1" satellite of the third moiety, and the intensity of the main isotope of the second moiety;

the intensity $M_5$ of the mass channel having the mass 104 is the sum of the intensity of the "+2" satellite of the first moiety, the intensity of the "+1" satellite of the second moiety, and the intensity of the main isotope of the third moiety; and the intensity $M_6$ of the mass channel having the mass 105 is the sum of the intensity of the "+2" satellite of the second moiety and the intensity of the "+1" satellite of the third moiety.

Figure 2:
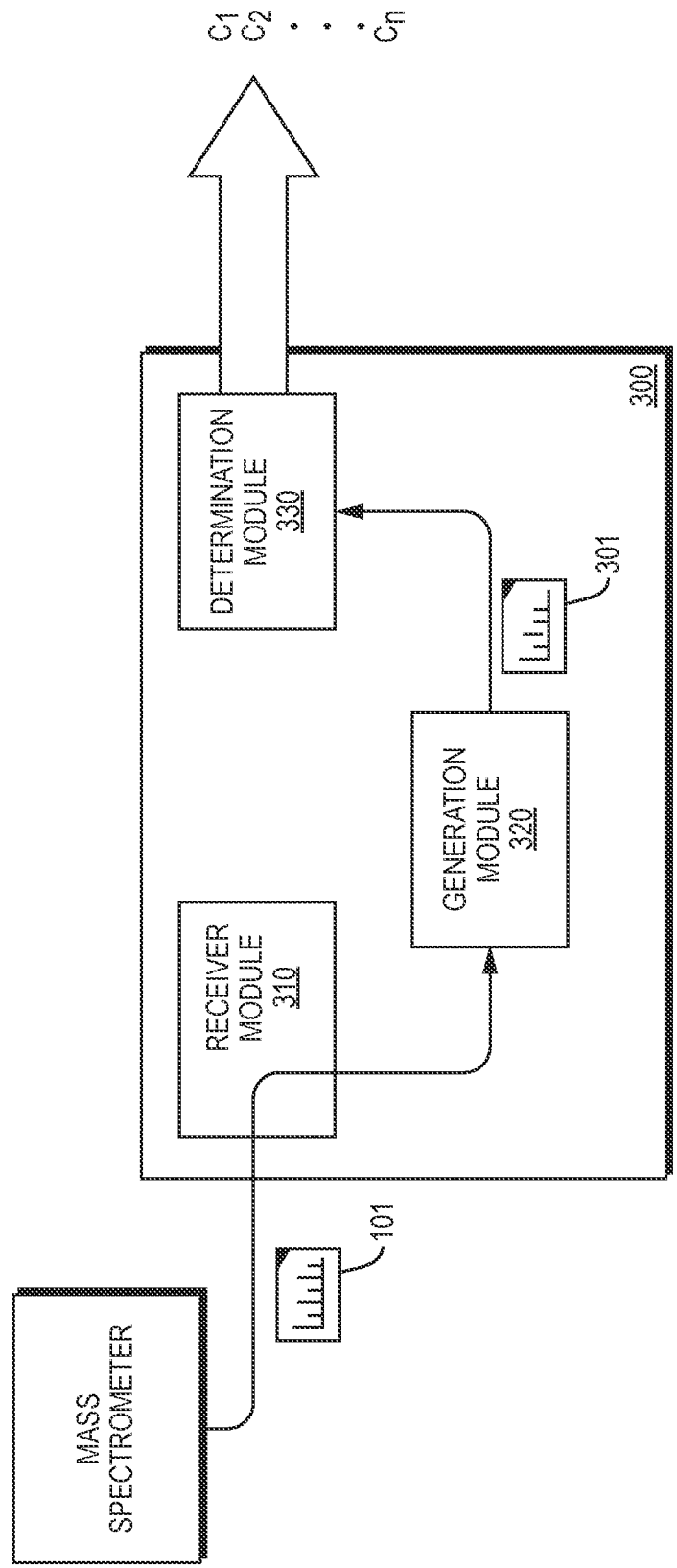
FIG. 2 schematically illustrates a logical arrangement of an example analysis system.

FIG. 2 schematically illustrates a logical arrangement of an example analysis system 300. The analysis system 300 comprises a receiver module 310, a mass spectrum data generation (or approximation) module 320, and a concentration determination module 330.

The receiver module 310 is arranged to receive mass spectrometry data 101. Typically, the receiver module 310 is arranged to receive the mass spectrometry data from a mass spectrometer coupled to (or connected to) the analysis system 300. However, it will be appreciated that the receiver module 310 may be arranged to receive the mass spectrometry data 101 from any suitable source, including a data storage device, a cloud computing service, a test data generation program etc. As set out previously, the mass spectrometry data 101 has a plurality of mass channels each having (or being filled with) a respective intensity (or intensity value).

The mass spectrum data generation (or approximation) module 320 is arranged to produce an approximated version 301 of the mass spectrometry data 101. The approximated version 301 of the mass spectrometry data comprises a set of mass channels. The set of mass channels of the approximate version 301 of the mass spectrometry data 101 typically correspond to the mass channels of the mass spectrometry data 101. In particular, for each mass channel of the mass spectrometry data 101 there may be a mass channel of the same mass present in the set of mass channels of the approximate version 301. It will be appreciated, however, that in some cases not all of the mass channels in the mass spectrometry data are taken account of. For example, as described above each molecular moiety has a respective quantification channel, which corresponds to the main mass of the isotopic pattern of said moiety. Where a set of expected moieties (and therefore corresponding quantification channels) have been identified for the mass spectrometry data, the set of mass channels of the approximated version 301 of the mass spectrometry data may comprise just those mass channels that correspond to the identified quantification channels.

In producing the approximated version 301, the mass spectrum data generation (or approximation) module 320 is arranged to iteratively fill the set of mass channels with chunks of intensity data. For a given iteration a fill of the set of mass channels is carried out according to the isotopic pattern of a molecular moiety selected for said iteration. Each chunk of intensity data comprises (or represents) an intensity to be distributed to the mass channels. The iterative filling is directed by the mass spectrum data generation module 320 so as to cause the approximated version 301 mass spectrometry data to converge towards the mass spectrometry data 101. Typically, the fill at a given iteration is determined based on a measure of discrepancy between the mass spectrometry data and the approximated version 301 of the mass spectrometry data at said iteration. In particular, the molecular moiety selected for a given iteration may be one which reduces the measure of discrepancy between the mass spectrometry data 101 and the approximated version 301 of the mass spectrometry data.

The mass spectrum data generation module 320 is configured to terminating generation of the approximated version 301 of the mass spectrometry data once a fitness criterion is met. The fitness criterion indicates a fit of the approximated version 301 of the mass spectrometry data to the measured mass spectrometry data 101. It will be appreciated that the fitness criterion may be adjusted (or set) by a user based on the desired accuracy of the approximated version 301 of the mass spectrum. Additionally, or alternatively, the fitness criterion may be set based on a known or estimated accuracy of the measured mass spectrometry data 101.

The concentration determination module 330 is arranged to determine the amount (or concentration) of at least one of the molecular moieties present (or represented) in the measured mass spectrometry data 101. The determination for a given molecular moiety is based on the total amount of fills (or total amount of intensity of the chunks of intensity data filled) according to the respective isotopic pattern of said molecular moiety.

Figure 3A:
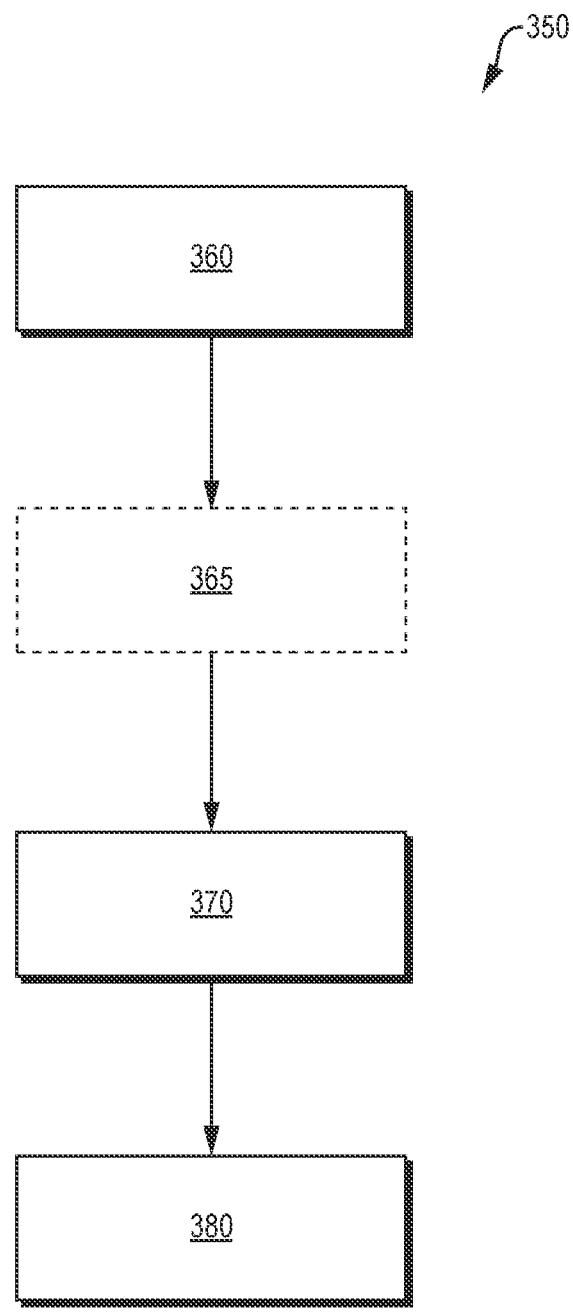
FIG. 3a schematically illustrates a method of deconvoluting measured mass spectrometry data that may be carried out (or implemented by) the analysis system shown in FIG. 2.

FIG. 3a schematically illustrates a method 350 deconvoluting measured mass spectrometry data 101 that may be carried out (or implemented by) the analysis system 300.

A step 360 comprises the receiver module 320 receiving mass spectrometry data 101.

An optional step 365 comprises the receiver module 320 identifying the molecular moieties represented in (or present in or contributing to) the received mass spectrometry data 101. The skilled person would be aware of a number of different ways in which this could be achieved. Typically, such as for example in mass tagging experiments, the moieties will be known or pre-determined by the way in which the experiment was carried out. Additionally, or alternatively the moieties present may be determined based on intensity peaks in the mass spectrometry data. It will be appreciated that identifying the molecular moieties may be considered equivalent to identifying the quantification channels, as the reporter mass of a given molecular moiety would be a known quantity.

A step 370 comprises the mass spectrum data generation (or approximation) module 320 iteratively filling a set of mass channels to produce an approximated version of the mass spectrometry data. For a given iteration a fill of the set of mass channels is carried out according to the isotopic pattern of a molecular moiety selected for said iteration. Each chunk of intensity data comprises (or represents) an intensity to be distributed to the mass channels. The iterative filling is directed by the mass spectrum data generation module 320 so as to cause the approximated version 301 mass spectrometry data to converge towards the mass spectrometry data 101. Typically, the fill at a given iteration is determined based on a measure of discrepancy between the mass spectrometry data 101 and the approximated version 301 of the mass spectrometry data at said iteration. In particular, the molecular moiety selected for a given iteration may be one which reduces the measure of discrepancy between the mass spectrometry data 101 and the approximated version 301 of the mass spectrometry data. In certain embodiments, the molecular moiety selected for a given iteration may be the one having a mass corresponding to the mass channel with the largest difference in intensity between the approximated version of the mass spectrometry data and the measured mass spectrometry data.

A step 380 comprises the concentration determination module 330 determining the amount of each molecular moiety that produced the measured mass spectrometry data 101 based on the total amount of fills according to the respective isotopic pattern of said molecular moiety. Generally the sum of the overall intensities of all of the chunks of intensity data filled for a particular selected moiety is (or is proportional to) the concentration of the moiety.

It will be appreciated that this can be determined in any one of number of different ways. For example, a set of quantification channels can be updated each time a fill is performed for the approximated version 301 of the mass spectrometry data as part of (or at the same time as) each fill in step 370. This may take the form of a running total such as $C_j=C_j+\Delta a$, where $\Delta a$ is the overall intensity of a chunk of intensity at a given fill step, the chunk of intensity being for the moiety having the quantification channel for $C_j$. Alternatively a record may be kept of the fills and the concentrations $C_i$ determined at step 380 by analysis of the record. For example, the number of fills for each moiety and with each total intensity may be kept. These counts may then be summed (weighted according to the respective total intensities) for each moiety to produce the concentrations for each moiety.

Figure 3B:
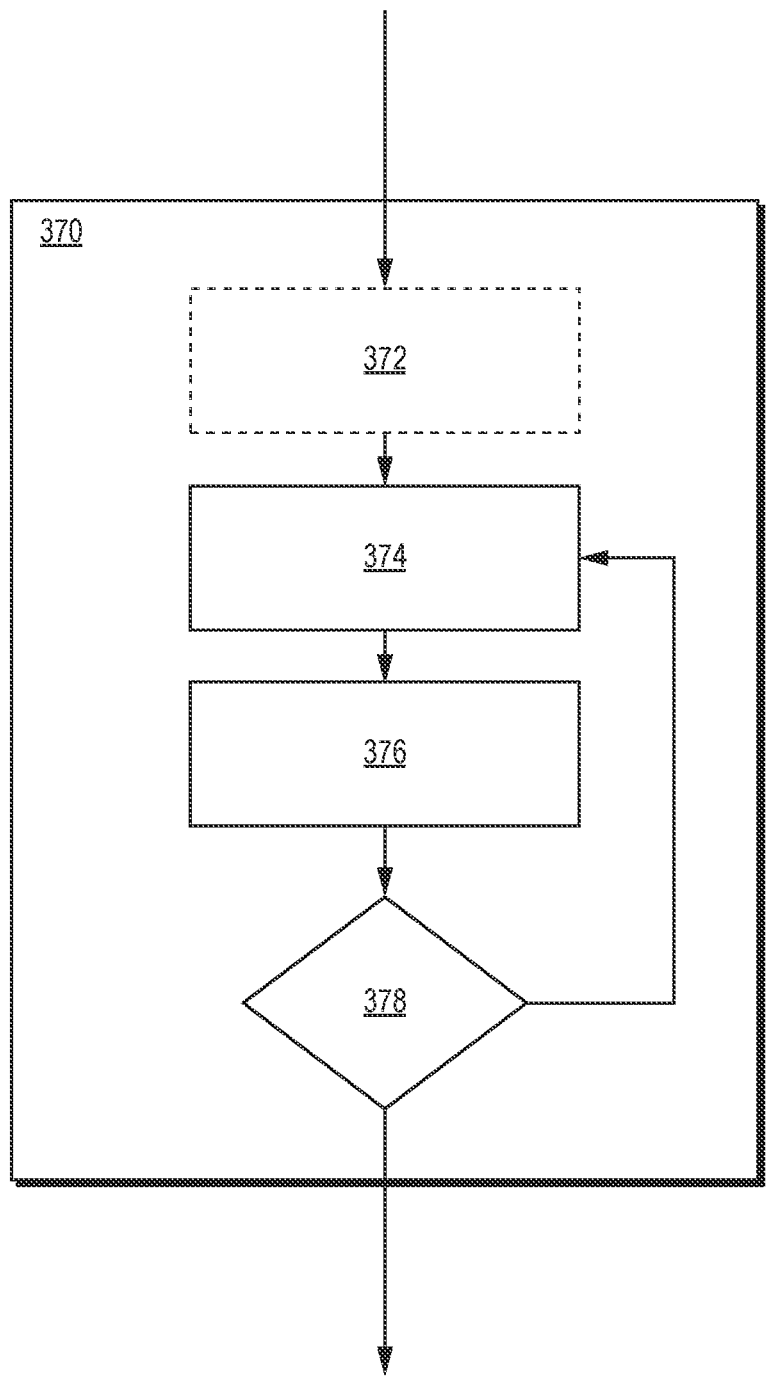
FIG. 3b schematically illustrates a variant of the iterative filling step of the method shown in FIG. 3a FIG. 4 shows isotope ratios for two quantitative channels.

The step 370 may comprise a number of sub steps as set out below in reference to FIG. 3b. FIG. 3b schematically illustrates a variant of the step 370 of the method 350 as shown in FIG. 3a. The step 370 may comprise a number of sub-steps as follows.

An optional sub step 372 comprises initializing the set of mass channels of the approximated version 301 of the mass spectrometry data. The sub step 372 may comprise including known or estimated background and/or noise into the set of mass channels. In particular known or estimated background and/or noise data may comprise respective (estimated) noise intensities for one or more of the mass channels of the set of mass channels. The set of mass channels may be filled with said noise data—i.e. having the noise intensities added to the intensity values for the corresponding mass channels. In the discussion that follows it will be appreciated that background typically refers to a constant (or reasonably constant) extraneous signal. This may be directly determined from other information (e.g. in chromatography—MS a signal that is present in all spectra). Noise typically refers to variable or fluctuating interference. For noise typically only statistical information is available. As such, in the described pre-filling preferably a statistical average of the noise may be used along with the full predicted background.

It will be appreciated that such a sub step has the advantage of allowing the method 350 to take account of known or estimated noise in the measured spectrometry data 101.

A sub step 374 comprises selecting a mass channel from the set of mass channels of the approximated version 301 of the mass spectrometry data. The mass channel may be selected based on a measure of discrepancy between the measured mass spectrometry data 101 and the approximated version 301 of the mass spectrometry data at said iteration. Typically, the mass channel corresponding to the largest discrepancy between the intensity of the measured mass spectrometry data 101 and intensity of the approximated version 301 of the mass spectrometry data is selected. It will be appreciated that any number of measures of discrepancy may be used. In particular, any suitable measure of discrepancy between the measured mass spectrometry data 101 and the approximated version 301 of the mass spectrometry data that is local with respect to mass may be used. An example would be an arithmetic difference between the intensities of the measured mass spectrometry data 101 and intensities of the approximated version 301 of the mass spectrometry data on a mass channel by mass channel basis. In this case the mass channel with the largest difference in intensity between the approximated version 301 of the mass spectrometry data and the measured mass spectrometry data 101 may be chosen.

It will be appreciated that the sub step 374 may be considered equivalent to selecting a molecular moiety based on the above discussed criteria. In particular, the moiety having a main mass (or reporter mass) that corresponds to the selected mass channel may itself be directly selected. As discussed above, in some cases there may be mass channels in the set of mass channels of the approximate version 301 of the mass spectrometry data that do not have corresponding molecular moieties (i.e. that do not have corresponding quantification channels). In such cases sub step 374 may be modified such that only the sub set of mass channels that do have corresponding quantification channels may be used.

Whilst the description herein of the method 350 is not cast in terms of a reward function it will be appreciated that some of the embodiments of the present invention may be thought of in this way. In particular, a reward scheme that gives in each filling step a reward that is proportional to the distance between measured and estimated intensity in the channel of the fill may be considered equivalent to the always filling the mass channel with the greatest discrepancy between the measured mass spectrometry data 101 and the approximated version 301 of the mass spectrometry data at said iteration. Alternatively, a reward scheme that returns as a reward the distance reduction between the measured mass spectrometry data 101 and the approximated version 301 of the mass spectrometry data at said iteration may start filling randomly and may lead to situations where a single channel has been overfilled and only "reverse filling" (i.e. subtractions) can lead to a minimal distance. The preceding reward function may be modified by penalizing overfill in general or specifically in a neighbouring channel.

A sub step 376 comprises filling the set of mass channels with a chunk of intensity data according to the isotopic pattern of the selected molecular moiety. As set out previously the chuck of intensity data typically has an overall intensity which is distributed to the mass channels according to the isotopic pattern of the selected molecular intensity. The overall intensity of each chunk of intensity data may be fixed across all iterations. Alternatively the overall intensity of each chunk of intensity data may be set based on the discrepancy determined in the corresponding sub step 374. Particular examples of such variation will be described shortly below. However, it will be appreciated that improved convergence speed of the iterative filling may be achieved if the overall intensity of the chunk of intensity data decreases monotonically with respect to decreasing determined discrepancy. This allows comparatively large chunks of intensity data (i.e. chunks of intensity data having comparatively large overall intensities) to be used to fill up the majority of each mass channel of the approximate version of the mass spectrometry data as it converges towards the measured mass spectrometry data 101.

By selecting the molecular moiety, and therefore the isotopic pattern that governs the fill in sub step 376, based on the discrepancy between the approximated 301 and measured 101 mass spectrometry data convergence of the approximated mass spectrometry data 301 to the measured mass spectrometry data 101 may be enforced. This is because overfilling of mass channels where the approximated mass spectrometry data is already close to the measured mass spectrometry data may be avoided. Additionally, or alternatively fills may be wholly or partially retracted (or subtracted) to compensate for detected overfilling. Such retraction of fills may be particularly advantageous when used in conjunction with variable chunk sizes and termination criteria that permit overfilling of mass channels, as larger chunk sizes may then be used promoting faster convergence. A sub step 378 comprises terminating the step 370 when a fitness criterion is met indicating a fit of the approximated version of the mass spectrometry data to the measured mass spectrometry data. It will be appreciated that there may be more than one fitness criterion, and that the termination may occur when any or all are satisfied. The termination criteria may comprise any one or more of the following being fulfilled: a total intensity contributed by the chunks of isotopic data equaling to the sum of the intensities for all mass channels in the measured mass spectrometry data 101 (typically, within a tolerance); no mass channel has a discrepancy measure (for example a difference) between the approximated version 301 and the measured mass spectrometry data 101 that is equal to or larger a predetermined threshold (which may be a minimum chunk size (or intensity); intensities in all mass channels of the simulation are within a predefined maximum tolerance compared to the measured mass spectrometry data. It will be appreciated that the maximum tolerance may vary according to mass channel. Additionally or alternatively the maximum tolerance is set based on known or estimated noise levels.

The sub steps 374; 376 may be iterated or repeated until termination occurs in the sub step 378.

In some variants an additional accept/reject test may be included as part of the filling sub step 374. In particular a fill may be rejected if it would cause the intensity of any of the mass channel of the approximated version 301 of the mass spectrometry data to exceed the corresponding intensity of the mass channel in the measured mass spectrometry data 101 by a pre-determined amount. In the case of such a rejection a fill may be attempted using a reduced size of chunk of intensity data. Additionally or alternatively, a fill may be attempted using moiety corresponding to the mass channel having the next highest discrepancy measure with respect to the measured mass spectrometry data 101. In such variants an additional termination criteria may also be used in the sub step 378 where termination occurs should fills be rejected for all mass channels or moieties.

The method of the invention can be implemented as one or more algorithms. The algorithms can be run on a computer. There could be many optimization schemes to improve efficiency of the method, for example based on the fact that peaks $M_1$ to $M_n$ in the measured mass spectrum 101 are typically a reasonably good approximation to the solutions, $C_q$.

In view of the above discussion of the generalized algorithm a preferred optimization process forms the spectrum approximation to the measured spectrum as follows:

- an approximated (or simulated) spectrum 301 is formed by iteratively filling the spectrum with chunks of isotopes (i.e. increasing the intensities of a number of mass channels commensurate with the effects of additional isotopes at those respective masses being introduced into the mass spectrum), wherein each chunk has the isotopic pattern or composition $S_j^i$ of one of the molecular moieties, i.e. one of the molecular moieties that corresponds to one of the mass channels. The size or intensity of the chunks depends on the desired accuracy of the method. Typically a chunk size (or overall intensity) of 0.1% to 1% of the most intense measured peak $M_p$ is sufficient but a chunk size could be lower or higher, e.g. as low as 0.01% or as high as 3, or even 10% of the most intense measured peak $M_p$. Chunk sizes can be higher than this, especially in embodiments where a variable chunk size is used, but a minimum size is typically at least 0.01% or 0.1% of the most intense measured peak $M_p$. Chunk sizes can be variable, for example the method may employ different chunk sizes for the respective molecular moieties depending on the intensity of the molecular moieties in the measured spectrum 101, and/or may employ different chunk sizes as the simulation progresses (e.g. starting with larger chunk sizes and reducing the size with filling of the simulation spectrum)
- at each step 374 (or each iteration of filling in the step 370) above, the mass channel with the largest difference between the simulated spectrum 301 and measured spectrum $M_p$ 101 is chosen for the next fill, i.e. the spectrum 301 is filled in that step with a chunk of isotopes that has the isotopic pattern or composition $S_j^i$ of the molecular moiety that corresponds to that mass channel. A fill attempt may be rejected if the resulting intensity of a peak in the approximated (or simulated) spectrum after filling is (or would be) higher than the measured intensity of the peak plus a predetermined tolerance t, which may be defined as an absolute or relative value on individual measured peaks $M_p$ or all $M_p$. As set out above this pre-determined tolerance may be based on an known or expected noise level, and may be specified per mass channel.
- the algorithm stops when attempts to add another chunk fail, i.e. are rejected, for all mass channels and/or when the total amount of intensity distributed in the chunks is equal to the sum of the intensities of the measured spectrum 101, plus optionally a tolerance, or when no mass channel has a difference between the simulation (i.e. the approximated version 301 of the mass spectrometry data) and the measured mass spectrometry data 101 or spectrum that is larger than or equal to the minimum chunk size used or when the intensities in all mass channels are within a predefined maximum variation compared to the measured mass spectrometry data 101 or spectrum, or when any two or more of these criterion are met.

From the amount or number of fills corresponding to each of the individual quantification channels are tracked or recorded and the sum of the fills for each channel is then assumed as the result, i.e. the concentration or amount of the molecular moiety $C_q$ corresponding to that mass channel.

Optionally the simulated spectrum may be "prefilled" with chunks representing known contributions of noise of background, which may then not be tracked for the purpose of determining the concentration $C_q$.

In some embodiments, a preferred optimization of the algorithm includes estimating "good" first fill values from the measured peak intensities $M_p$ [e.g. (Max($M_p$−2 Max(li, ri), 0)] where li, ri are left or right interferences based on assuming that the neighbouring $M_q$ are equal to the corresponding $C_q$ with the isotope pattern $S_j^q$. It will be appreciated that a "left interference" refers to the contribution to a given mass channel of the +1 satellite of the moiety having a main mass corresponding to the mass channel to the immediate left. For example for the mass channel for $M_i$ the left interference would be $S_i^{i-1}C_{i-1}$. Similarly the right interference would be $S_i^{i+1}C_{i+1}$. The assumption made in the example optimization is to use the adjacent measured intensities $M_{i-1}$ and $M_{i+1}$ as if they were the moiety concentrations $C_{i-1}$ and $C_{i+1}$ respectively.

In some embodiments, a preferred optimization may include starting the fills with a larger chunk size (or total intensity) and reducing the chunk size as the simulated spectrum approaches the measured. A larger chunk size is weighted more than smaller chunk size when determining the result, i.e. the concentration or amount of the molecular moiety $C_q$. For example, a chunk size that is 3× larger than a smaller chunk size would count 3× as much towards the concentration, i.e. it would be effectively counted as 3 smaller chunks for determining the result, i.e. the concentration or amount of the molecular moiety.

The method may provide the following advantages: the computational effort for the method is proportional to n*F*Q, where n is the number of contributing patterns/moieties, F is the maximum number of peaks per moiety and Q is the quality, i.e. the expected number of distribution steps for the highest signal. As Q and F are constant this means that the computational effort in "Big O notation" (https://en.wikipedia.org/w/index.php?title=Big_O_notation&oldid=898399272) is of the order $O_n$ (also written as O(n)), i.e. for a growing number of contributions (i.e. moieties) to take into account the effort grows linearly with the number of contributions/moieties, as opposed to e.g. a conventional solution using a matrix inversion with the Gauss-Jordan method or a singular value decomposition which have a computational effort that scales with the number of contributors to the power of three, i.e. $O_{n^3}$ (also written as $O(n^3)$). This makes it advantageous, for example, for deconvoluting mass spectra comprising peaks from a large number of moieties, such as TMT sets with a large number of tags, e.g. 6, 10, 11, 16 or more tags; the method guarantees that no results less than zero are generated, which is a common issue when using general purpose mathematical solutions; the method is tolerant to noise in the mass spectrum and known noise levels can be used for determination of a reasonable termination criterion (e.g. tolerance t), i.e. a noise level in the measured mass spectrometry data can be used for determination of the defined tolerance used in the termination criterion of the simulation; a known background intensity in the measured spectrum or data can be easily accommodated by pre-filling the simulated spectrum with the background intensity before starting the iterative method of the invention.

In certain embodiments, the invention may be viewed as effectively interpreting the mass spectrometry experiment, such as a mass tag quantification experiment, as a Markovian model. A nondeterministic Markov Chain (Markov Decision Process, MDP) may be defined that contains all parameters of the quantification experiment, i.e.

The number of quantification channels (mass channels)

The "impurities" of each channel from other channels in the experiment

Impurities due to channels that are not present in the current experiment

Any sources of noise

Then, the measurement using mass spectrometry, as well as steps such as a chemical labelling step of peptides performed in the laboratory, can be seen as executing a simulation according to the probabilistic distributions and connections of a Markov Decision Process (MDP) that precisely represents the experiment. Further details of such an approach are described in more detail below.

Impurities due to channels that are not present in the current experiment may be:

Satellites of channels that are quantified, but where these satellites don't interfere with other channels channels present in the sample (thus convoluting the spectra) but not being quantified in the current deconvolution method.

Similar to the collection of ions over time to form spectra, which may be viewed as a Poisson process, where at every time an ion is collected with a probability according to the isotope ratios of the tags and the intensity ratios are given by the relative concentrations, the Markov chain places in every step a set of intensities into the different masses according to the isotope ratios of the tags, and choosing the channel based on the maximum distance to the measured spectrum ensures that the probabilities of adding intensities to a channel are the same as in a Poisson process.

While the method of always filling the channel with the largest distance to the measured spectrum first is especially advantageous and ensures that the optimization always approaches the correct concentrations from "the bottom", other schemes, such as a round robin scheme where peaks are visited in any order, e.g. by mass number, and just no chunk is added when the difference between measured and simulated data is less than a predetermined amount will work as well, but may require removal of chunks in the process, such that the simulated spectrum "oscillates" towards the correct solution. Oscillating approximations are faster, but are usually less preferred for accuracy and stability reasons. The preferred method of the invention is a special case of a non-negative optimization.

In order to enable a more detailed understanding of the invention, various embodiments will now be described. It should be understood that the scope of the invention is not limited to such embodiments, which are examples only.

Since the invention relates to mass spectrometry data, the term mass herein refers to mass (m) to charge (z) ratio (m/z), which is the same value as the mass for singly charged ions.

As an illustration of the invention, first a very simple hypothetical example is described:

Assume the quantification channels have the following properties, for simplicity just using nominal mass:

Quantification Channel 1 (for example representing the mass of a first mass tag (Tag 1)): main mass: 100, having one satellite at mass 101, intensity of the satellite: 10%. In other words the isotopic pattern of the moiety Tag 1 may be written as $S_{+1}^{Tag\ 1}=0.1$ and $S_0^{Tag\ 1}=1$.

Quantification Channel 2 (for example representing the mass of a second mass tag (Tag 2)): main mass: 101, having one satellite at mass 100, intensity of this "left" or "−1" satellite: 5%, and having another satellite at mass 102, intensity of this "right" or "+1" satellite: 7%. In other words the isotopic pattern of the moiety Tag 2 may be written as $S_{+1}^{Tag\ 2}=0.07$, $S_{-1}^{Tag\ 2}=0.05$ and $S_0^{Tag\ 2}=1$.

Figure 4:
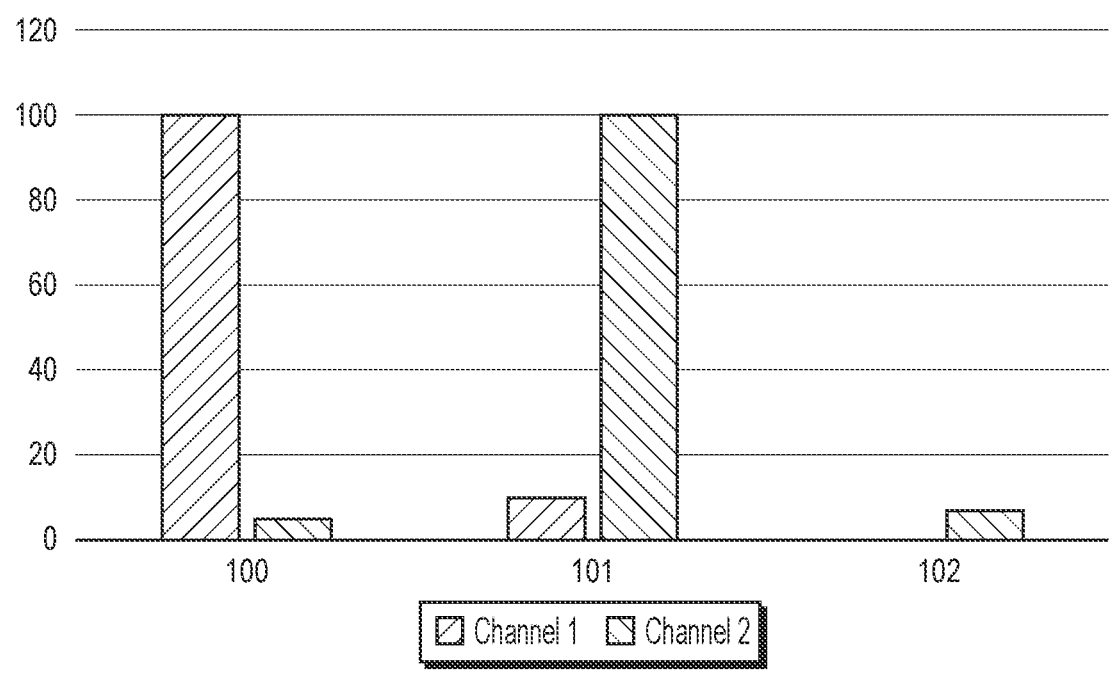

Symbolized as bar graphs, these quantification channels are shown in FIG. 4.

In this case the quantification channels are normalized such that the most intense signal in each channel has an intensity of 100% (or "1.0"). That is the sum of all masses/ions in the channel is 100% (from the main mass 100)+10% (from the impurity at mass 101=110% for the Tag 1 channel, centered at m/z 100, and 5%+100%+7%=112% for Tag 2, which is Channel 2, with main mass m/z 101; relative to the intensity of the most intense m/z in the channel. This is a common representation for impurities of mass tags in the accompanying documentation for commercial tags such as TMT tags distributed by Thermo Fisher Scientific, Inc. An alternative normalization is such that the sum of all peaks is 100% (or, especially for representation in a software program, the normalization is such that the sum of the intensities of all mass peaks in the channel is 1.0 in the unit of the calculation). It is important for correct quantitation to keep in mind that the sum of all peaks is representative for the amount of labelled substance in a sample.

Figure 5:
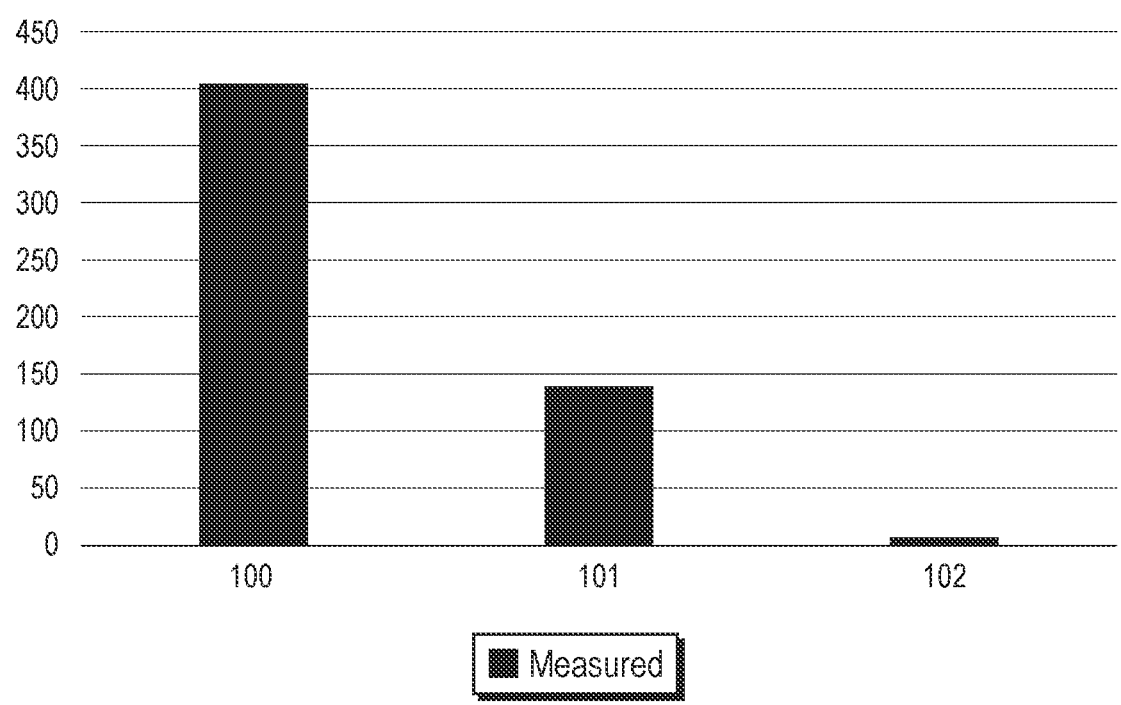
FIG. 5 shows intensities of a measured mass spectrum from a known ratio of the channels.

A measurement from a mass spectrometry experiment where two samples have been labelled with the quantification channels (Tags) 1 and 2 respectively is shown in FIG. 5.

The measured intensities are 405 at mass (or mass channel) 100, 140 at mass (or mass channel) 101 and 7 at mass (or mass channel) 102.

While this hypothetical example measurement is noise free and an equation system of the type of (eq. 1) may be immediately solved due to the impurity in the 102 mass channel, which is not part of the experiment and must—as can be seen in FIG. 4—be due to quantification channel 2, this may be approximated by the inventive method:

It can be immediately seen how the quantification channels would grow by e.g. filling with chunks having a size of 1.0 each at their main peak, thus this example for the sake of brevity directly illustrates an accelerated method:

The method comprises the preferred approach of filling always the peak with the largest difference between simulated and measured first. This can be easily seen when starting with a quick fill with larger chunks, which advantageously starts at the largest measured signal.

In a first step, an algorithm may insert a quick start chunk based on an estimation of the maximum interferences of neighbouring peaks:

At mass channel 100 the main signal (or intensity) from quantification channel 1 is expected. The only neighbour is at mass channel 101. In a worst case approximation of the interference from quantification channel 2 we would assume that all intensity at mass channel 101 is from quantification channel 2. Then the interference at mass 100 would be 140 (the measured intensity at mass 101) times 5/100 (the relative intensity of the left side peak of quantification channel 2)=7. Optionally a safety margin of e.g. 1.5 times, 2 times, 3 times or 4 times may be applied, but in this case it is known that there is no interference to the measurement at m/z 100 from the other side, and thus no additional safety margin is applied and the expected worst case interference is just rounded to 10.0 and quantification Channel 1 (along with the corresponding mass channels) may be pre-filled with a first large chunk:

The measured intensity is 405, the estimated worst case interference is 10, thus:

Chunk 1: 395 at mass 100 and 39.5 at mass 101 from quantification channel 1.

Similarly we may now look at quantification channel 2, with a measured intensity of 140 at mass 101.

We take into account that the mass channel 101 is already pre-filled with an intensity of 39.5 from quantification channel 1. Thus an upper bound for any pre-fill in this channel is 140−39.0−5=100.5.

Another upper bound may be found by looking at the possible interferences: We know that there is only a possible interference from the "+1" peak of the m/z 100 mass channel. Thus another upper bound for any pre-fill is 10% of the signal at m/z 100, which is 405, thus the upper bound is 140-40.5=99.5, which may be rounded downwards to 99.

Thus we can fill quantification channel 2 (along with the corresponding mass channels) with a chunk:

Chunk 2: 99 at mass 101, 4.95 at mass 100 and 6.93 at mass 102.

Figure 6:
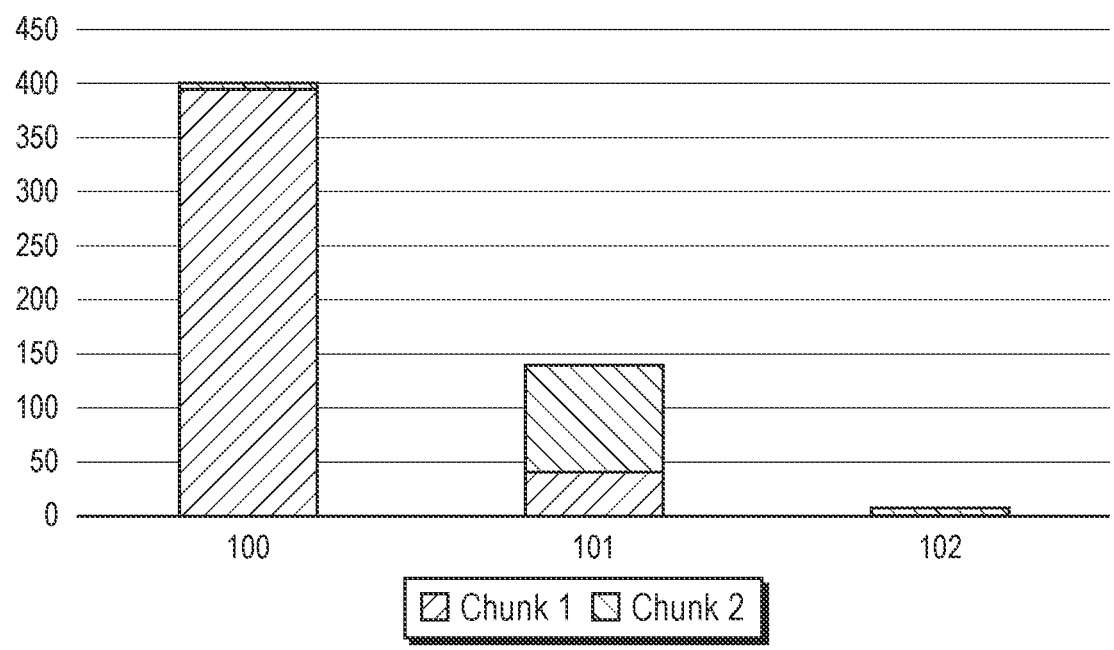
FIG. 6 shows an example for simulating with variable chunk size, the first two chunks being approximated using worst case assumptions about interferences from neighbouring channels.

The simulated (or approximated) spectrum now looks as shown in FIG. 6 and has intensities of 399.95 at m/z 100, 138.5 at m/z 101 and 6.93 at m/z 102.

The collected intensities so far are

Quantification Channel 1: 395+39.5=434.5 (from Chunk 1)

Quantification Channel 2: 99+4.95+6.93=110.88 (from Chunk 2).

Now the iteration may be continued in steps of 1, and e.g. to a summed spectrum with a tolerance of 1.

Figure 7A:
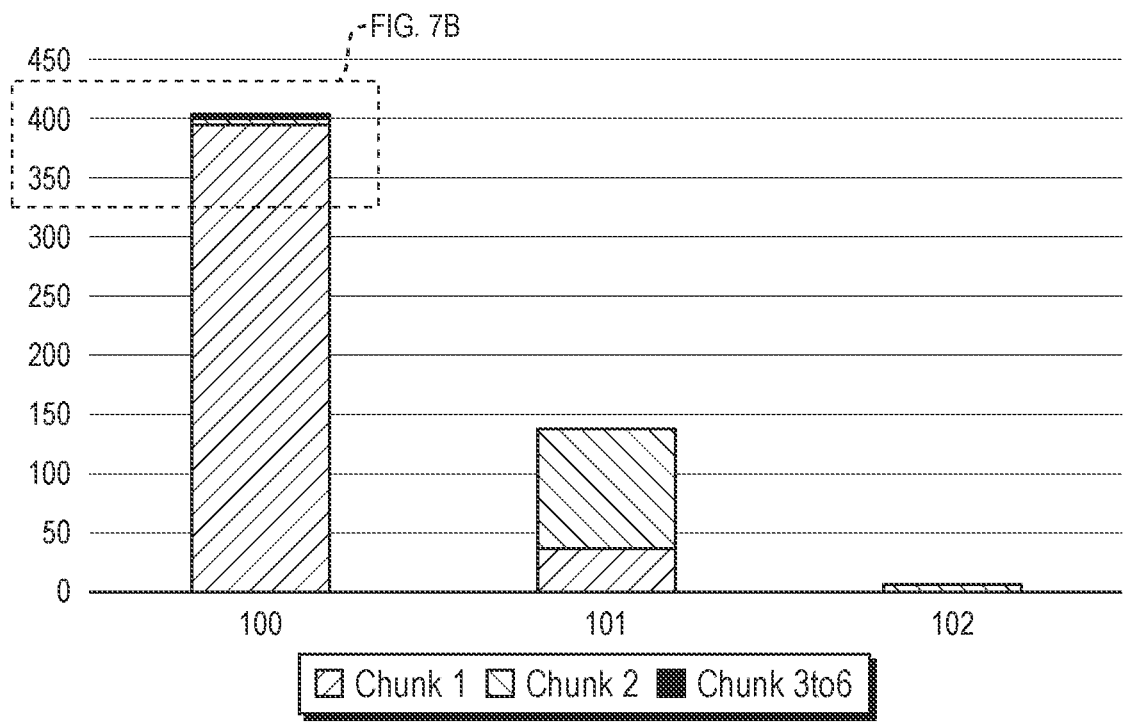
FIG. 7 shows the result of continuing the simulation of FIG. 6 with four more steps of equal size.
Figure 7B:
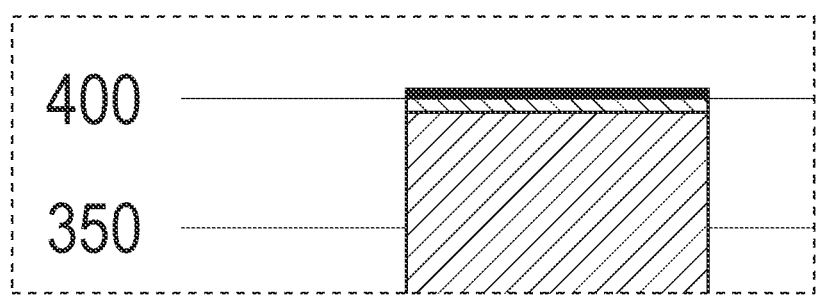

The difference between measured and simulated at m/z 100 is 5.05 and at m/z 101 it is 1.5. Thus the next chunk of size 1 at the main signal goes into Channel 1:

Chunk 3 (Quantification Channel 1): 1 at mass 100, 0.1 at mass 101. The difference is still largest at m/z 100, thus Chunk 4 (Quantification Channel 1): 1 at mass 100, 0.1 at mass 101 And Chunk 5 (Quantification Channel 1): 1 at mass 100, 0.1 at mass 101, And Chunk 6 (Quantification Channel 1): 1 at mass 100, 0.1 at mass 101, Giving a simulated spectrum of:

403.95 @m/z 100, 138.9 at m/z 101 and 6.93 at m/z 102. (FIG. 7)

Now the largest difference to measured is 1.1 at m/z 101 compared to 1.05 at m/z 100.

Accordingly:

Chunk 7 (Quantification Channel 2): 1 at mass 101, 0.05 at mass 100 and 0.07 at mass 102, Giving a simulated spectrum of:

404 @m/z 100, 139.9 at m/z 101 and 7.00 at m/z 102.

And a final chunk goes to quantification channel 1:

Chunk 8 (Quantification Channel 1): 1 at mass 100, 0.1 at mass 101,

Giving exactly the measured spectrum as a result.

We may now collect the intensities from the chunks:

Quantification Channel 1: Chunks 1, 3, 4, 5, 6, 8: 434.5+5*1.1=440

Quantification Channel 2: Chunks 2, 7: 110.88+1.12=112

Giving the input ratio of 3.93 (rounded to 2 figures).

A second example now illustrates a tandem mass tag labelling workflow.

Figure 8:
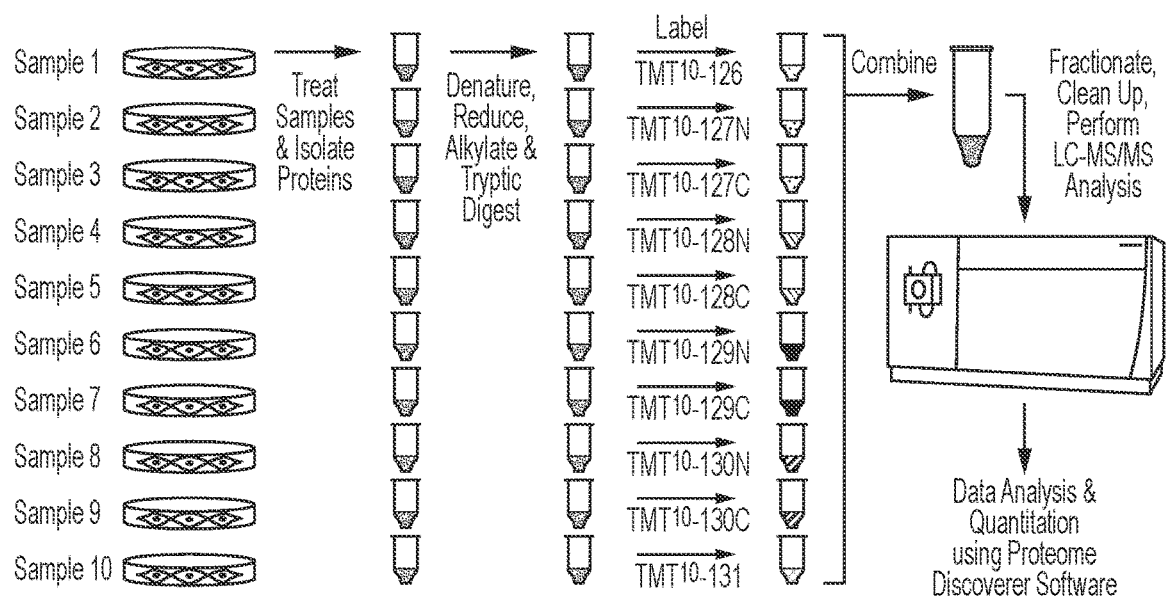
FIG. 8 is a simplified overview of a quantitative experiment with tandem mass tags (TMT).
Figure 8:
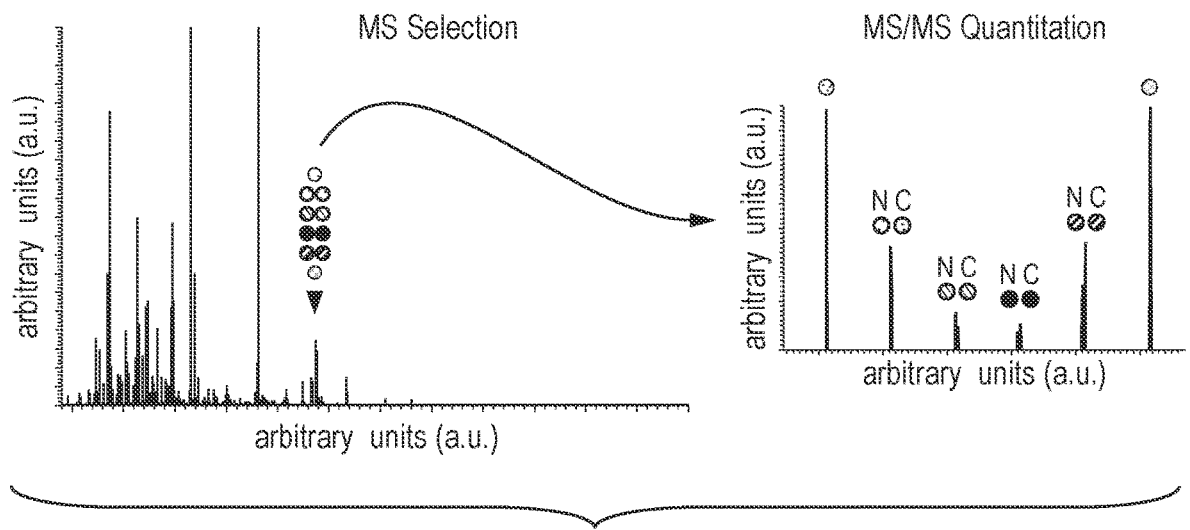

A set of samples, eg. protein extracts isolated from cells or tissues, is pre-treated, including digestion of the proteins and then each sample is reacted with one of the labels, as shown in FIG. 8. After labelling the samples are mixed and analyzed by high resolution Orbitrap™ LC-MS/MS.

Figure 9:
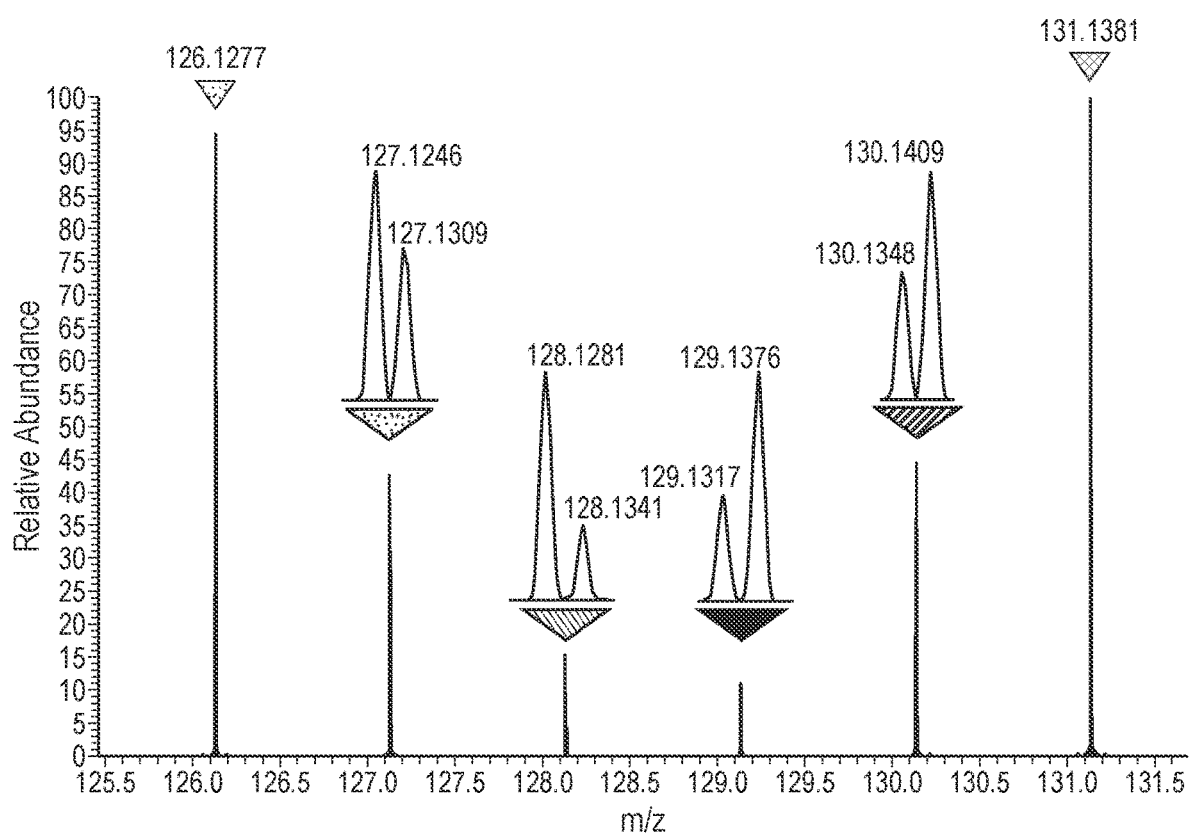
FIG. 9 shows an example of a single $MS^2$ spectrum in the tag region (enlarged from bottom right of FIG. 8).

FIG. 9 shows an example of 10-plex relative quantification using TMT10plex Reagents. BSA tryptic digests labelled with TMT10plex reagents (TMT10 126-131 Da) were mixed 16:8:4:2:1:1:2:4:8:16 and analyzed by high resolution (Orbitrap LC-MS). The relative abundance of the target protein or peptide fragment in ten different samples is measured by comparing the reporter ions generated by MS/MS fragmentation of the different mass tags with the method of the invention as illustrated in the first example, using tag information as illustrated in table 1.

Measurements may be by data dependent or data independent analysis. In data dependent analysis e.g. the most intense precursor ions at any time step may be fragmented and a post-processing method may look for identifiable peptides and label ions in the resulting $MS^2$ spectra, which may e.g. look as shown in FIG. 9 in the label region.

The evaluation of peptide ratios from the different samples, each represented as a channel may then be performed for every $MS^2$ spectrum from every recognized peptide that has label information. Information from peptides may then be collected over the complete chromatography run and is aggregated to protein information with known methods. A protein ratio may e.g. be the median of the ratios of the peptides associated with the protein.

Frequently, as in the example above, the goal of the experiment is ratio determination, but absolute quantities may be generated when one of the channels has a known concentration. Such experiments with "internal standards" are e.g. known from the EPA method 1613 for Dioxin analysis and many other similar methods. The method of this invention is applicable to such experiments.

The following shows an example of the invention described as a Markov model (Markov Decision Process, MDP) and with pseudo-code:

Defining the Experiment-MDP

Let $M=\{M_1, M_2, \ldots, M_n\}$ be a measured spectrum, where $M_i$ represents the intensity of the i-th peak of the spectrum. We say that this measured peak corresponds to a reporter quantification channel i. Furthermore, let $I_M$ be the summed (total) intensity over all peaks in the spectrum. Accordingly, let $C=\{C_1, C_2, \ldots, C_n\}$ be the intensities of the corrected spectrum (i.e. $C_i$ is the concentration of the moiety having its main mass at the mass channel i), and $I_C$ the corresponding summed intensity of said corrected spectrum. For ease of discussion we have assumed the scenario where every mass channel has a corresponding quantification channel—i.e. intensities in the measured spectrum that only result from satellite isotopes are ignored or discarded. The skilled person would appreciate that the MDP would also apply where this is not the case—i.e. where $M=\{M_1, M_2, \ldots, M_m\}$ and $C=\{C_q | q \in A, A \subset \{1, 2, \ldots, m\}, A \neq \emptyset\}$.

Figure 10:
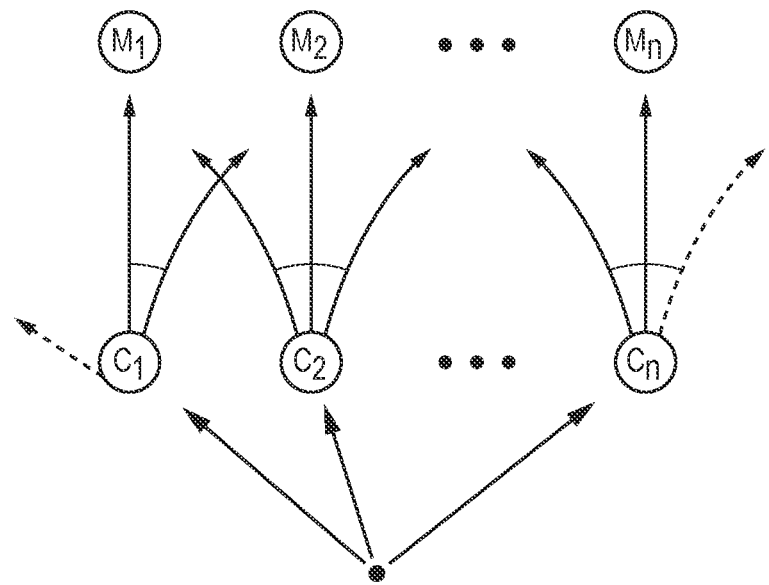
FIG. 10 shows a Markov Decision Process (MDP) that models the correction process.

The labelling experiment can be modelled by an MDP as shown in FIG. 10. In this Markov Decision Process MDP= (S, Act, ->, $s_0$) the states $S=\{M_1, \ldots, M_n, C_1, \ldots, C_n\}$ represent measured and corrected intensities of mass channels 1, ..., n. Moreover, the mass channels are associated by a transition relation ->:S×Act->Distr(S) that may be non-deterministic or probabilistic. The set of actions is needed to have both nondeterministic and probabilistic steps in the MDP, but we do not name the actions here. In the interpretation of the MDP as the quantification experiment, the impurity between channel i and j is modelled by a probabilistic distribution represented by the according probability function $P(i,j)$, $0 \leq P(i,j) \leq 1$. Note, that $P(i,j)$ corresponds to the coefficients $S_j^i$ of equation 1 above.

A solution to the said deconvolution problem then means to calculate set of corrected peak intensities $\{C_i: 1 \le i \le n\}$, such that the measured intensities become $\{M_j: 1 \le j \le n\}$ with respect to the constraint $$M_i = \sum_{i=A}^{n} C_i \cdot P(i, j)$$

for all j.

EXAMPLE

Consider a three-channel experiment with the following impurities:

|  | −2 | −1 | 0 | +1 | +2 |
|---|---|---|---|---|---|
| Quantification Channel #1 | 5% | 10% | 83% | 2% | — |
| Quantification Channel #2 | 2% | 4% | 92% | 1% | 1% |
| Quantification Channel #3 | 2% | 3% | 92% | 1% | 2% |

Figure 11:
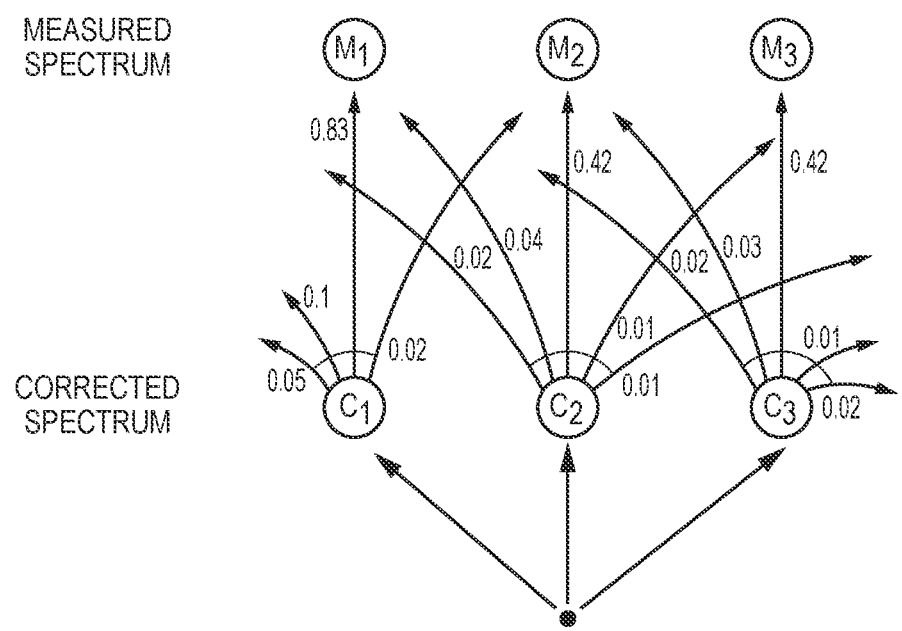
FIG. 11 shows a Markov Descision Process structure for a three-channel experiment.

Then the corresponding Markov Descision Process has the structure shown in FIG. 11. So, a spectrum C={C1, C2, C3} with intensities C1=100.0, C2=200.0, C3=500.0 would imply measured peaks M={M1, M2, M3} where $M1 = C1*0.83 + C2*0.04 + C3*0.02$ $M2 = C1*0.02 + C2*0.92 + C3*0.03$ $M3 = C2*0.01 + C3*0.92.$ A scheme is now described that can be used to simulate the quantification experiment with the MDP defined above:

---
Scheme 1: Simulate Reporter Quantification Experiment

1     Label n samples of peptides,
         yielding $A_i$, $1 \le i \le n$ numbers of labelled peptide molecules.
2     For all masses m
3          While $A_k > 0$ for any $1 \le k \le n$
4            Pick a sample (= mass channel) i where $A_i > 0$
5            Add intensity of one molecule to $C_i$
6            Utilize dice to determine j according to P(i, .)
7            Add intensity of one molecule to $M_j$
8            $A_i = A_i - 1$
9          End while
10    End for

---

In step 2, only those masses need to be used that are present in the actual samples, and the dice in step 6 are a symbol for an arbitrary selection process that is probabilistic in the sense that it picks a destination channel j according to distribution P(i,.).

This type of probabilistic scheme may be implemented in a variant of method 350 as discussed above. In particular in this scheme at the sub step 376 the chunk of intensity data comprises (or is) a single intensity value. The intensity value may be the intensity of one or more molecules of the molecular moiety. The intensity value is filled in (or added to) a single mass channel selected according to a probability distribution (such as a probability mass function) based on (or comprising) the isotopic pattern of the selected molecular moiety. As such the selection of the single mass function may be regarded as a stochastic selection and is such that over an ensemble of fills of the same molecular moiety the resulting intensity increase of the mass channels of the approximated version of the mass spectrometry data will reflect (or comprise or otherwise follow) the isotopic pattern. It will also be appreciated that when implementing the sub step 376 a true source of entropy is not required and instead a suitably robust pseudorandom number generator of a suitable computer system may be used.

Solution Algorithm

The algorithm which approximates simulation Scheme 1 efficiently is now described in a more practical context with ample precision. For this Scheme 1 is modified to work with "chunks" of amounts of molecules/peptides rather than with single peptide molecules. Note, that according to the simulation scheme it holds that $I_M = I_C$, i.e., the summed intensity of spectrum M equals the summed intensity of spectrum C. This leads to a simple termination criterion (line 2) in the following procedure:

---
Procedure 1: Approximate Solution

Input: $I_M$
Output: Spectra C' and M' (approximated counterparts of C and M)

1     $R = I_M$
2     While(R > 0)
3         Pick peak $C'_i$
4         Fix an intensity amount $\Delta a$ of molecules
5         $C'_i = C'_i + \Delta a$
6         For each $1 \le j \le n$
7            $M'_j = M'_j + \Delta a * P(i, j)$
8         End for
9         $R = R - \Delta a$
10    End While

---

It can be shown easily that for step 3, the very peak $C'_i$ can be selected that features the largest corresponding remaining difference in M, i.e., the i where $|M_i - M'_i|$ is maximal over all i. This is discussed in detail with above in reference to FIGS. 3a and 3b.

Moreover, a suitable value of $\Delta a$ (the overall intensity of the chunk of intensity data) depends on how close the approximated solution should be to the exact solution that can be determined by standard matrix inversion. E.g., if $\Delta a = I_M / 1e06$, the overall precision of the solution will be 1 ppm of the overall spectrum intensity. Note, that with respect to various noise sources in the real experiment, the precision of the solution needs not to exceed the inherent noise level of the experiment.

It is evident from Procedure 1 that all solutions $C'_i, C_q$ are positive (or zero). Approximated spectra are built up by only adding values to the peak intensities $C'_i$ and $M'_i$. Furthermore, the method is stable against noise sources since the termination criterion only aims at using the whole intensity amount of the measured spectrum M and is tolerant against noise errors since it always improves the peak with the largest current error.

This type of deterministic scheme may be implemented in a further variant of method 350 as discussed above. In particular in this scheme at the sub step 376 the chunk of intensity data comprises a set of intensities each corresponding to a respective mass channel. The set of intensities is scaled according the isotopic pattern for the intensity data. In other words the intensity for a given mass channel comprises (or is equal to or is proportional to) the overall intensity of the chunk of intensity data scaled by the component of the isotopic pattern corresponding to the same mass channel. Using the notation set out previously for a given mass channel i the intensity may follow $M_i \propto S_i^j \Delta C_j$ where $\Delta C_j$ is the overall intensity of the chunk of intensity data (written as $\Delta a$ previously), which corresponds to the increase in the quantification channel for $C_j$ for that particular fill.

Many improvements or variants of the method are possible, for example the step size may vary continuously, known background or other ions may be used before the iterations start, the step size may be chosen in a way that is informed about the signal to noise ratio (S/N) of the peaks, e.g. when the largest signal has a S/N of 20 it is not necessary to have steps significantly smaller than the noise level (i.e. 1/20th of the maximum signal) because a higher resolution of the simulation is not justified by the information content of the spectrum.

The probabilistic approach is well aligned with a model for ion collection.

Embodiments of the invention provide a method of deconvolution of mass spectrometry data comprising overlapping isotopic distributions with high tolerance and adjustment to situations where noise and background is present, which scales well and is thus suitable for experiments with a high number of simultaneous mass tags.

It will be appreciated that embodiments of the invention may be used in respect of proteomics experiments. A typical proteomics experiment with TMT quantitation contains an LC-MS experiment after the labelling and other sample preparation steps. In the typical quantitation experiment a data dependent mechanism may be performed that identifies potentially labelled peptides (typically by assuming that everything is a labelled peptide and selecting ions by intensity), selects them for fragmentation and performs a fragment ion "scan". In most TMT data evaluations the mass tags themselves are measured in the mass tag region of the spectrum and for each single (putative) peptide spectrum the ratios between the tags are determined. Data dependent strategies are usually geared towards measurement of as many different peptides as possible. As the goal of the measurement is quantitation of proteins, the individual ratios determined for the measured peptides are then collected to generate overall ratios for the proteins comprising the measured peptides. These methods are well known in the art and not discussed here.

In case of data independent analysis (DIA) the methods usually aim at having more than one fragment spectrum per peptide across chromatographic peaks. In such cases it is advantageous (but not required) to use chromatographic peak areas for the determination of labelling ratios.

While the determination of label intensities is usually performed in the "label fragment region", it is possible to look for the "other half" of the labels in the remainder of the spectrum. This is especially advantageous when accidentally more than one peptides was isolated and fragmented.

Embodiments of the invention may be used for deconvolution of charge states of multiply charged molecules in high resolution spectra.

A commonly known algorithm for deconvolution of electrospray spectra is described in >>D. M. Horn, R. A. Zubarev, and F. W. McLafferty, "Automated reduction and interpretation of high resolution electrospray mass spectra of large molecules," *Journal of the American Society for Mass Spectrometry*, vol. 11, no. 4, pp. 320-332, 2000.

This is an example of what we may call a subtractive algorithm: A predicted pattern is recognized in the measured data, scaled, and then the recognized portion is subtracted from the measured data. This procedure is repeated until the original data are consumed. In this case the potential isotopic patterns are approximated as averagine (i.e. an average peptide) ions. Averagine ions with matching mass and charge are checked for fit quality and if they match the subtraction is initiated.

The main disadvantages to such subtraction methods are that frequently the first matches are scaled too high, that the remainders are more and more prone to false fitting into noise, and that only one candidate is compared to the data at a time.

In order to improve accuracy such a subtractive approach (such as that in Horn et al.) may be used as an input to the method of the invention resulting in a list of candidate moieties that may then be used for the iterative method of the invention. While TMT deconvolution is typically a well-defined process, the deconvolution of electrospray data may suffer from ambiguity at higher masses (typically a plus/minus one error). In that case instead of the purely deterministic approach that is preferred for TMT deconvolution a more probabilistic approach is preferred, and multiple non-deterministic simulations with random variations of the averagine masses around those estimated from a determination of the mass and charge by distance of the exact masses and fit of distribution may be advantageous. If a deterministic method is desired all likely combinations may be fully estimated. The estimation with the highest similarity score would then be selected as the final estimation.

The use of any and all examples, or exemplary language ("for instance", "such as", "for example" and like language) provided herein, is intended merely to better illustrate the invention and does not indicate a limitation on the scope of the invention unless otherwise claimed. No language in the specification should be construed as indicating any non-claimed element as essential to the practice of the invention.

As used herein, including in the claims, unless the context indicates otherwise, singular forms of the terms herein are to be construed as including the plural form and vice versa. For instance, unless the context indicates otherwise, a singular reference herein including in the claims, such as "a" or "an" means "one or more".

Throughout the description and claims of this specification, the words "comprise", "including", "having" and "contain" and variations of the words, for example "comprising" and "comprises" etc, mean "including but not limited to", and are not intended to (and do not) exclude other components.

The present invention also covers the exact terms, features, values and ranges etc. in case these terms, features, values and ranges etc. are used in conjunction with terms such as "about", "around", "generally", "substantially", "essentially", "at least" etc. (e.g., "about 3" shall also cover exactly 3, or "substantially constant" shall also cover exactly constant).

The term "at least one" should be understood as meaning "one or more", and therefore includes both embodiments that include one or multiple components. Furthermore, dependent claims that refer to independent claims that describe features with "at least one" have the same meaning, both when the feature is referred to as "the" and "the at least one".

Any steps described in this specification may be performed in any order or simultaneously unless stated or the context requires otherwise.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

It will be appreciated that the methods described have been shown as individual steps carried out in a specific order. However, the skilled person will appreciate that these steps may be combined or carried out in a different order whilst still achieving the desired result.

It will be appreciated that embodiments of the invention may be implemented using a variety of different information processing systems. In particular, although the figures and the discussion thereof provide an exemplary computing system and methods, these are presented merely to provide a useful reference in discussing various aspects of the invention. Embodiments of the invention may be carried out on any suitable data processing device, such as a personal computer, laptop, personal digital assistant, mobile telephone, set top box, television, server computer, etc. Of course, the description of the systems and methods has been simplified for purposes of discussion, and they are just one of many different types of system and method that may be used for embodiments of the invention. It will be appreciated that the boundaries between logic blocks are merely illustrative and that alternative embodiments may merge logic blocks or elements, or may impose an alternate decomposition of functionality upon various logic blocks or elements.

It will be appreciated that the above-mentioned functionality may be implemented as one or more corresponding modules as hardware and/or software. For example, the above-mentioned functionality may be implemented as one or more software components for execution by a processor of the system. Alternatively, the above-mentioned functionality may be implemented as hardware, such as on one or more field-programmable-gate-arrays (FPGAs), and/or one or more application-specific-integrated-circuits (ASICs), and/or one or more digital-signal-processors (DSPs), and/or other hardware arrangements. Method steps implemented in flowcharts contained herein, or as described above, may each be implemented by corresponding respective modules; multiple method steps implemented in flowcharts contained herein, or as described above, may be implemented together by a single module.

It will be appreciated that, insofar as embodiments of the invention are implemented by a computer program, then a storage medium and a transmission medium carrying the computer program form aspects of the invention. The computer program may have one or more program instructions, or program code, which, when executed by a computer carries out an embodiment of the invention. The term "program" as used herein, may be a sequence of instructions designed for execution on a computer system, and may include a subroutine, a function, a procedure, a module, an object method, an object implementation, an executable application, an applet, a servlet, source code, object code, a shared library, a dynamic linked library, and/or other sequences of instructions designed for execution on a computer system. The storage medium may be a magnetic disc (such as a hard drive or a floppy disc), an optical disc (such as a CD-ROM, a DVD-ROM or a BluRay disc), or a memory (such as a ROM, a RAM, EEPROM, EPROM, Flash memory or a portable/removable memory device), etc. The transmission medium may be a communications signal, a data broadcast, a communications link between two or more computers, etc.

Annex

To further aid understanding of the invention and its mathematical basis we provide below an alternative derivation of the above discussed Markov Chain. This alternative derivation is described with reference to "impurities" (defined shortly below) but it will be appreciated that this alternative derivation is equivalent to those discussed above.

Firstly, again we note that the measured spectrum $S_{Mea}$ (referred to in the preceding discussion as M) may be written as:

$$S_{Mea} = \{M_1, M_2, \ldots, M_n\}$$

where $M_j$ are the peaks of the spectrum and $1 \leq j \leq n$. The abundance values of the reporter peaks $M_1, \ldots, M_n$ are denoted as $A(M_j)$, where $A(M_j) \in \mathbb{R}_{>0}$. In this discussion we refer to the reporter channels (as discussed previously) as c, where $c \in \{1, \ldots, n\}$ Let $i_{s,d}$ be the so-called impurity channel s (source) to channel d (destination) in the sense that it reflects that probability that a reporter molecule randomly picked from vial of channel s is in fact from channel d—i.e. the probability that a randomly selected reporter molecule according to a mass tag with a main mass in channel s is an isotopologue having a mass in channel d. As will be appreciated this probabilistic interpretation of an impurity resembles the interpretation discussed above in the background section where the impurity is instead viewed as an isotopic distribution Slot the mass tag.

Likewise, a spectrum of theoretical peaks and their abundances (may be defined as)

$$S_{Theo} = \{T_1, T_2, \ldots, T_n\}$$

where $T_j$ are the peaks of the spectrum and $1 \leq j \leq n$. The abundance values of the theoretical peaks $T_1, \ldots, T_n$ are denoted as $A(T_j)$—i.e. the estimated abundances for each mass tag corresponding to each reporter channel, where $A(T_j) \in \mathbb{R}_{>0}$. It will be appreciated that these abundances may be considered equivalent (to within a constant scaling factor) to the concentrations $C_j$ of the mass tags described previously.

The theoretical peaks may then be related to the measured spectrum as follows:

$$A(M_1) = i_{1,1} \cdot A(T_1) + i_{2,1} \cdot A(T_2) + \ldots + i_{n,1} \cdot A(T_n)$$
$$A(M_2) = i_{1,2} \cdot A(T_1) + i_{2,2} \cdot A(T_2) + \ldots + i_{n,2} \cdot A(T_n)$$
$$\vdots$$
$$A(M_n) = i_{1,n} \cdot A(T_1) + i_{2,n} \cdot A(T_2) + \ldots + i_{n,n} \cdot A(T_n)$$

As before this can be recast as a matrix equation:

$$IT = M$$

-continued $$\text{where } I = \begin{pmatrix} i_{1,1} & i_{2,1} & i_{3,1} & \cdots & i_{n,1} \\ i_{1,2} & i_{2,2} & i_{3,2} & \cdots & i_{n,2} \\ i_{1,3} & i_{2,3} & i_{3,3} & \cdots & i_{n,3} \\ \vdots & \vdots & \vdots & \ddots & \vdots \\ i_{1,n} & i_{2,n} & i_{3,n} & \cdots & i_{n,n} \end{pmatrix},$$

$$T = \begin{pmatrix} A(T_1) \\ A(T_2) \\ A(T_3) \\ \vdots \\ A(T_n) \end{pmatrix},$$

$$M = \begin{pmatrix} A(M_1) \\ A(M_2) \\ A(M_3) \\ \vdots \\ A(M_n) \end{pmatrix}$$

As discussed above in relation to eq. 1 this matrix equation may be solved for the vector T of theoretical peaks—the estimated channel abundances (or mass tag concentrations) through the use of known methods like the Gaussian algorithm, SV or LU decomposition or various approximations.

An improved approach according to the present invention instead may follow the following derivation, using a Markov Chain formalism.

We construct a Markov Chain from the real experimental setting that re-creates the reporter ions quantification experiment for a single spectrum as a Markov Chain. This Markov Chain $\mathcal{M}_{full}$ contains the parameters from the experiment, i.e., the probabilities that a peptide is from a particular channel $c \in \{1, \ldots, n\}$ in the experiment, the probabilities that this peptide has been labelled incorrectly with a tag from a different channel $c' \in \{1, \ldots, n\}$, $c' \neq c$ due to an impurity.

It thus contains the chemical labelling step of peptides performed in the laboratory and allows for virtually picking molecule by molecule (labelled peptide) for the measurement in the mass spectrometer summing up the corresponding abundance values for the theoretical spectrum as well as for the measured spectrum.

The Complete Experiment Markov Chain $M_{full}$

As before we assume an experiment with n channels. We define a Markov Chain $\mathcal{M}_{full} = (S, \text{Pur}, \text{Imp}, s_0)$ where S is a set of states $S = \{s_0, T_1, T_2, \ldots, T_n, M_1, M_2, \ldots, M_n\}$, $s_0 \in S$ is the starting state, Pur: $\{s_0\} \rightarrow \text{Distr}(\{T_1, T_2, \ldots, T_n\})$ is a probabilistic transition function reflecting the pure labelling.

Imp: $\{T_1, T_2, \ldots, T_n\} \rightarrow \text{Distr}(\{M_1, M_2, \ldots, M_n\})$ is a transition function reflecting the impurities.

Figure 12:
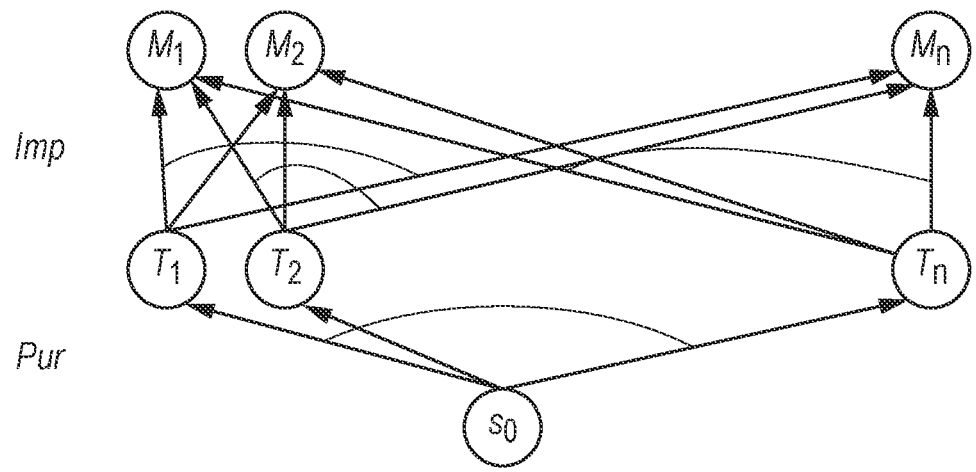
FIG. 12 shows a Markov Chain structure.

For the actual probability to reach a particular state with Pur or Imp, we write, e.g., $\text{Pur}(s_0, T_j)$ or $\text{Imp}(T_j, M_k)$. A graphical representation of the state transition can be seen in FIG. 12. As above we define a general abundance function $A: S \rightarrow \mathbb{R}_{>0}$ that assigns to every state (peak) in S an abundance value.

Note that there is a probabilistic distribution Pur between the starting state $s_0$ and the theoretical peaks $T_i$ and a probabilistic distributions Imp for the transition of the theoretical peaks to the measured. We choose Pur according to the true distribution of the channels in the actual sample that is measured with the mass spectrometer and Imp according to the impurities. For this consider the following example.

Assume the following quantification experiment:
n=3 (3 channels),
75% of the molecules are labelled with channel 1,
20% are labelled with channel 2, and
5% are labelled with channel 3.

Then if we use the probability distribution $\text{Pur}(s_0, T_1) = 0.75$, $\text{Pur}(s_0, T_2) = 0.2$ and $\text{Pur}(s_0, T_3) = 0.05$ accordingly to the percentage values given above and assign the overall abundance (i.e., the total amount of labelled molecules in the sample) of $A(s_0) = 100$ to the starting state.

We then can calculate the expected abundances of peaks $T_1, \ldots, T_3$ in the Markov Chain through applying probability laws, resulting in, $$A(T_1) = A(s_0) \cdot \text{Pur}(s_0, T_1) = 100 \cdot 0.75 = 75$$

$$A(T_2) = A(s_0) \cdot \text{Pur}(s_0, T_2) = 100 \cdot 0.2 = 20$$

$$A(T_3) = A(s_0) \cdot \text{Pur}(s_0, T_3) = 100 \cdot 0.05 = 5$$

Furthermore, adding the information of arbitrary impurities I to the calculations the abundance values $A(T_1), \ldots, A(T_3)$ can be applied as probabilistic transitions $\text{Imp}(T_j, M_j)$ as follows:

$$A(M_1) = \text{Imp}(T_1, M_1) \cdot A(T_1) + \text{Imp}(T_2, M_1) \cdot A(T_2) + \text{Imp}(T_3, M_1) \cdot A(T_3)$$

$$A(M_2) = \text{Imp}(T_1, M_2) \cdot A(T_1) + \text{Imp}(T_2, M_2) \cdot A(T_2) + \text{Imp}(T_3, M_2) \cdot A(T_3)$$

$$A(M_3) = \text{Imp}(T_1, M_3) \cdot A(T_1) + \text{Imp}(T_2, M_3) \cdot A(T_2) + \text{Imp}(T_3, M_3) \cdot A(T_3)$$

Here $i_{s,d}$ equals $\text{Imp}(T_s, M_d)$.

Note that this also resembles the linear equation system explained earlier above.

We now describe a stepwise algorithm that can be used to simulate the quantification experiment with $\mathcal{M}_{full}$ "molecule by molecule".

Scheme 1: Simulate Reporter Quantification Experiment

Input: $M_{partial}$
Output: Abundances of M and T.

1. Start with given $M_{full}$, let $A_{all}$ be the summed abundance of all molecules of the measured spectrum. Start with $A(s) = 0$ for any state s of $M_{full}$.
2. While $A(s_0) < A\_all$
3.    Add abundance of one molecule to $A(s_0)$
4.    Determine successor state $T_j$ according to $\text{Pur}(s_0)$
5.    Add intensity of one molecule to $A(T_j)$
6.    Determine successor state $M_k$ according to $\text{Imp}(T_j)$
7.    Add intensity of one molecule to $A(M_k)$
8. End while It will be appreciated that at the end of the simulation we have $$A_{all} = A(s_0) = \sum_{1 \leq j \leq n} A(T_j) = \sum_{1 \leq j \leq n} A(M_j)$$

i.e., the initial abundance in the starting state is fully distributed to the theoretical (or estimated) and the measured spectrum.

This particular algorithm relies on $M_{full}$ being known in which case the distribution $Pur(s_0)$ immediately reflects the quantification. However, as set out below we can construct a second algorithm where this distribution is, as it is in reality, unknown.

The Partial-Knowledge Markov Chain $\mathcal{M}_{partial}$

As mentioned above in the experimental setting only the measured peaks M are given along with the impurity coefficients I that had an imprint on the experiment. The theoretical peaks T are, until then, unknown. Calculation of T remains the problem to be solved. Since the probabilistic distribution $Pur(s_0)$ would now be unknown it is replaced for the sake of modelling by a non-deterministic decision, leading to a partial-knowledge Markov Chain or Markov Decision Process.

Figure 13:
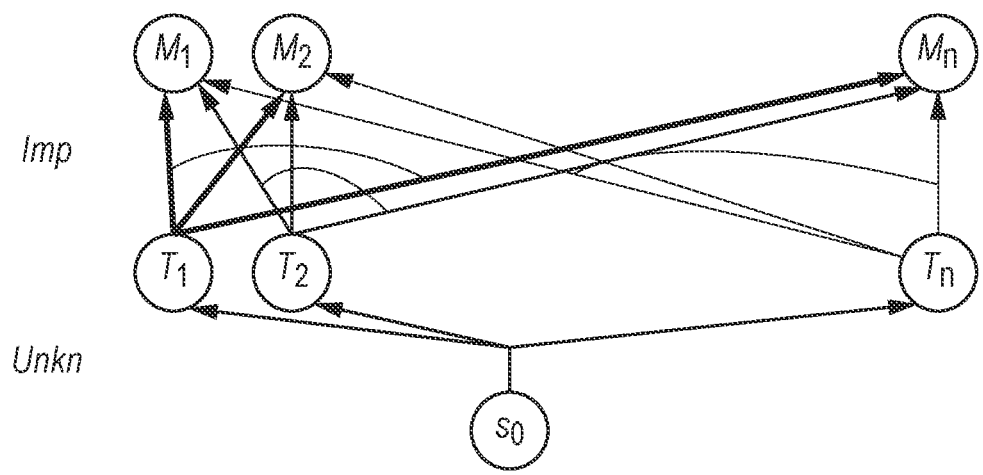
FIG. 13 shows a further Markov Descision Process structure.

We define a Markov Decision Process $\mathcal{M}_{partial}=(S,Unkn,Imp,s_0)$ where $S=\{s_0, T_1, T_2, \ldots, T_n, M_1, M_2, \ldots, M_n\}$ is the set of states, $Pur: \{s_0\} \rightarrow Distr(\{T_1, T_2, \ldots, T_n\})$ is the probabilistic transition function that assigns every theoretical peak the probability to go to a particular successor state in M due to an impurity, so is the starting state and Unkn is a function that non-deterministically selects a theoretical peak when starting in $s_0$. The structure of this Markov Decision Process is shown graphically in FIG. 13. This particular structure models the known impurity factors as a probabilistic distribution, but the now unknown theoretical peaks as a nondeterministic choice for $T_1, \ldots, T_n$ when starting in $s_0$.

Solution Algorithm for $\mathcal{M}_{partial}$

We can now construct an algorithm analogous to Scheme 1 but in the context of $\mathcal{M}_{partial}$, whilst still providing ample precision. For this we modify Scheme 1 to work with "chunks" of abundances rather than with single molecules.

---

Procedure 1
===========================================================

Input: $M_{partial}$
Output: Abundances of M and T.
===========================================================

Start with given $M_{partial}$, let $A_{all}$ be the summed
   abundance of all molecules. Start with A(s) = 0 for any
   state s of $M_{partial}$.
1    While $A(s_0) < A_{all}$
2        Pick channel j
3        Fix an intensity amount Δa of molecules (a "chunk")
4        $A(T_j) = A(T_j) + \Delta a$
5        For each k: 1 ≤ k ≤ n
6            $M_j = Mk + \Delta a * Imp(T_j, M_k)$
7        End for
8        R = R − Δa
9    End While

---

It will be appreciated that steps 2 and 3 in the above algorithm together form the action of Unkn. An example of how these may be carried out is as follows. Assume an observed spectrum $S_{Obs}=\{O_1, O_2, \ldots, O_n\}$ with its observed abundances A(Oj). Channel j can be selected where $|M_j-O_j|$ is maximal over all channels at any state of the algorithm. A suitable value of Δa in step 3 may depend on how close the approximated solution should be to the exact solution that can be determined by solving the linear equation system. For example, as set out previously, if $\Delta a = A_{all}/1e06$, the overall precision of the solution will be 1 ppm of the overall spectrum intensity. It will be appreciated that with respect to various noise sources in the real experiment, the precision of the solution needs not to exceed the inherent noise level of the experiment.

Various examples are set out below in the following numbered paragraphs (NP)

NP1. A method for deconvoluting measured mass spectrometry data comprising overlapping isotopic patterns of at least two molecular moieties, comprising:
   identifying a plurality of mass channels within the mass spectrometry data that correspond to the masses of the molecular moieties;
   producing a simulation of the measured mass spectrometry data by iteratively filling the mass channels with chunks of isotopic data, wherein each chunk comprises the isotopic pattern of one of the molecular moieties;
   terminating the simulation when a fitness criterion is met for the mass channels indicating a fit of the simulation to the measured mass spectrometry data; and
   determining the amount of each molecular moiety that produced the measured mass spectrometry data based on the total amount of fills in the simulation with the isotopic pattern of each molecular moiety.

NP2. The method according to NP1, wherein at each iteration, the chunk of isotopic data used for filling comprises the isotopic pattern of the molecular moiety having a mass corresponding to the mass channel with the largest difference in intensity between the simulated mass spectrometry data and the measured mass spectrometry data.

NP3. The method according to NP1 or NP2, further comprising rejecting a fill from the simulation if it results in the intensity in a mass channel of the simulated mass spectrometry data being greater than the intensity in the mass channel of the measured mass spectrometry data above a defined tolerance.

NP4. The method according to any preceding NP, wherein the fitness criterion is met by any of the following:
   (i) when filling is rejected for all mass channels;
   (ii) when a total intensity contributed by the chunks of isotopic data is equal to the sum of the intensities for all mass channels in the measured mass spectrometry data or spectrum;
   (iii) when no mass channel has a difference between the simulation and the measured mass spectrometry data that is equal to or larger than a minimum chunk size;
   (iv) when intensities in all mass channels of the simulation are within a predefined maximum tolerance compared to the measured mass spectrometry data NP5. The method according to any preceding NP, wherein the size of each chunk is selected depending on the desired accuracy of the method.

NP6. The method according to any preceding NP, wherein the size of each chunk is 0.1% to 1% of the most intense measured peak $M_p$ in the measured mass spectrometry data.

NP7. The method according to any preceding NP, wherein the simulation comprises starting the fills with chunks of isotopic data of a larger size and reducing the chunk size as the simulation approaches the measured mass spectrometry data.

NP8. The method according to NP4, wherein a noise level in the measured mass spectrometry data is used for determination of the defined tolerance used in the fitness criterion of the simulation.

NP9. The method according to any preceding NP, wherein prior to iteratively filling the mass channels with chunks of isotopic data, the simulation is pre-filled with a known background intensity of the measured mass spectrometry data.

NP10. The method according to any preceding NP, wherein the molecular moieties are mass tags or fragments derived from mass tags.

NP11. The method according to NP10, wherein the molecular moieties are tandem mass tags or fragments derived from tandem mass tags.

NP12. The method according to NP11, wherein the molecular moieties are mass reporter moieties of tandem mass tags.

NP13. A computer program, stored on a computer-readable medium, which, when executed by one or more processors, causes the one or more processors to carry out the method according to any preceding NP.

The invention claimed is:

1. A method for deconvoluting measured mass spectrometry data, the method comprising:
    receiving measured mass spectrometry data representing at least two molecular moieties each having a respective isotopic pattern, wherein at least two of said isotopic patterns overlap;
    iteratively filling a set of mass channels to produce an approximated version of the mass spectrometry data, said iterative filling comprising a number of iterations, each iteration comprising filling one or more of the mass channels with a chunk of intensity data according to the isotopic pattern of a respective one of the two or more molecular moieties selected for said iteration, wherein for each iteration the chunk of intensity data is an intensity for a respective mass channel, wherein the respective mass channel is selected according to a probability distribution based on the isotopic pattern for the intensity data;
    terminating said iterative filling when a fitness criterion is met indicating a fit of the approximated version of the mass spectrometry data to the measured mass spectrometry data; and
    determining the amount of each molecular moiety that produced the measured mass spectrometry data based on the total amount of fills according to the respective isotopic pattern of said molecular moiety.

2. The method according to claim 1 wherein for each iteration the chunk of intensity data comprises a set of intensities each corresponding to a respective mass channel, wherein the set of intensities is scaled according the isotopic pattern for the intensity data.

3. The method according to claim 1 wherein the molecular moiety selected for each iteration is selected based on a measure of discrepancy between the measured mass spectrometry data and the approximated version of the mass spectrometry data at said iteration.

4. The method according to claim 1, wherein at each iteration, the molecular moiety having a mass corresponding to the mass channel with the largest difference in intensity between the approximated version of the mass spectrometry data and the measured mass spectrometry data is selected.

5. The method according to claim 1, further comprising rejecting a fill if it results in the intensity in a mass channel of the approximated version of the mass spectrometry data being greater than the intensity in the mass channel of the measured mass spectrometry data above a defined tolerance.

6. The method according to claim 1, wherein the size of each chunk is selected depending on the desired accuracy of the method.

7. The method according to claim 1, wherein the size of each chunk is 0.1% to 1% of the most intense measured peak $M_p$ in the measured mass spectrometry data.

8. The method according to claim 1, wherein the size of the chunks of isotopic data at each iteration decrease as the approximated version of the mass spectrometry data approaches the measured mass spectrometry data.

9. The method according to claim 1, wherein a noise level in the measured mass spectrometry data is used for determination of the defined tolerance used in the fitness criterion.

10. The method according to claim 1, wherein prior to iteratively filling the mass channels with chunks of isotopic data, mass channels the approximated version of the mass spectrometry data are pre-filled with a known background intensity of the measured mass spectrometry data.

11. The method according to claim 1, wherein the molecular moieties are mass tags or fragments derived from mass tags.

12. The method according to claim 1, wherein the molecular moieties are tandem mass tags or fragments derived from tandem mass tags, optionally wherein the molecular moieties are mass reporter moieties of tandem mass tags.

13. A computer program product comprising one or more non-transitory computer-readable media having computer programs instructed stored therein, the computer program instructions being configured such that, when executed by one or more computing devices, the computer program instructions cause the one or more computing devices to:
    receive measured mass spectrometry data representing at least two molecular moieties each having a respective isotopic pattern, wherein at least two of said isotopic patterns overlap;
    iteratively fill a set of mass channels to produce an approximated version of the mass spectrometry data, said iterative filling comprising a number of iterations, each iteration comprising filling one or more of the mass channels with a chunk of intensity data according to the isotopic pattern of a respective one of the two or more molecular moieties selected for said iteration, wherein for each iteration the chunk of intensity data is an intensity for a respective mass channel, wherein the respective mass channel is selected according to a probability distribution based on the isotopic pattern for the intensity data;
    terminate said iterative filling when a fitness criterion is met indicating a fit of the approximated version of the mass spectrometry data to the measured mass spectrometry data; and
    determine the amount of each molecular moiety that produced the measured mass spectrometry data based on the total amount of fills according to the respective isotopic pattern of said molecular moiety.

14. A system, comprising:
    one or more processors and memory configured to:
    receive measured mass spectrometry data representing at least two molecular moieties each having a respective isotopic pattern, wherein at least two of said isotopic patterns overlap;
    iteratively fill a set of mass channels to produce an approximated version of the mass spectrometry data, said iterative filling comprising a number of iterations, each iteration comprising filling one or more of the mass channels with a chunk of intensity data according to the isotopic pattern of a respective one of the two or more molecular moieties selected for said iteration, wherein for each iteration the chunk of intensity data is an intensity for a respective mass channel, wherein the respective mass channel is selected according to a probability distribution based on the isotopic pattern for the intensity data;

terminate said iterative filling when a fitness criterion is met indicating a fit of the approximated version of the mass spectrometry data to the measured mass spectrometry data; and determine the amount of each molecular moiety that produced the measured mass spectrometry data based on the total amount of fills according to the respective isotopic pattern of said molecular moiety.

\* \* \* \* \*